United States Patent [19]

Davis et al.

[11] Patent Number: 5,789,599
[45] Date of Patent: Aug. 4, 1998

[54] AZIRIDINE COMPOUNDS, METHODS OF PREPARATION AND REACTIONS THEREOF

[75] Inventors: Franklin A. Davis, Lower Merion; Ping Zhou; Gaddampally Venkat Reddy, both of Philadelphia, all of Pa.

[73] Assignee: Drexel University, Philadelphia, Pa.

[21] Appl. No.: 239,097

[22] Filed: May 6, 1994

[51] Int. Cl.[6] .................................................. C07D 203/24
[52] U.S. Cl. ........................ 548/965; 548/956; 548/957; 548/955
[58] Field of Search ............................ 548/965, 956, 548/957, 955

[56] References Cited

FOREIGN PATENT DOCUMENTS 2948832  6/1981  Germany ............................ 548/965

OTHER PUBLICATIONS

Anet, F.A.L. et al., "Electrophilic Substitution at Saturated Carbon. XXXI. Effects of Attached Second–Row Elements on the Rates of Nitrogen Inversion in Aziridines", *J.Am. Chem. Soc.* (1967) 89:2, pp. 357–361.

Baldwin, J.E. et al., "Nucleophilic Ring Opening of Aziridine–2–Carboxylates with Wittig Reagents; An Enantioefficient Synthesis of Unsaturated Amino Acids", *J. Chem. Soc. Chem. Commun.* (1987) pp. 153–155.

Baldwin, J.E. et al., "The Ring Opening of Aziridine–2–Carboxylate Esters with Organometallic Reagents", *J. Chem. Soc. Chem. Commun.* (1989) pp. 1852–1854.

Baldwin, J.E. et al., "Amino Acid Synthesis via Ring Opening of N–Sulphonyl Aziridine–2–Carboxylate Esters with Organometallic Reagents", *Tetrahedron* (1993) 49:28, pp. 6309–6330.

Bergmeier, S.C et al., "Chirospecific Synthesis of (1S, 3R)–1–Amino–3–(hydroxymethyl)cyclopentane, a Precursor for Carbocyclic Nucleoside Synthesis. Intramolecular Aziridine Cyclizations", *J. Org. Chem.* (1993) 53:18, pp. 5019–5022.

Bodenan, J. et al., "Acid–Catalyzed Ring Opening of 2–Substituted Aziridines with Alcohols", *Synthesis* (Mar. 1992), pp. 288–292.

Bongini, A. et al., "Iodocyclofunctionalization of (Z)–1–Trichloroacetimidoyloxyalk–2–enes and 3–Tri–Chloracetimidoyloxyalk–1–enes. Synthesis of (±)–erythro–Sphinganine Triacetate and (±) threo–Sphinganine Triacetate", *J. Chem. Soc. Perkin Trans.* (1986) 1, pp. 1339–1344.

Bouayad, Z. et al., "The Regioselectivity of the Ring Opening of 1–Activated or Nonactivated 2–Alkoxycarbonyl or 2–Cyanoaziridines by Carbanions of the Dicarbonyl Compounds", *J. Heterocyclic Chem.*, (Nov. 1991) 28, pp. 1757–1767.

Cainelli, G. et al., Studies on N–Metallo Imines: Synthesis of N–unsubstituted Aziridines From N–Trimethylsilyl Imines and Lithium Enolates of α–Halo Esters, *Tetrahedron Lett.*, (1991) 32:1, pp. 121–124.

Chervin, I.I. et al., "Asymmetric nitrogen. 57. NMR Study of the stereochemistry ...", *Izv. Akad. Nauk SSSR, Ser. Khim* (1988), 5, p. 1110–1121, *Chem. Abstr.* (1989) 110:56755g, (1 page).

Chilmonczyk, Z. et al., "121. Diastereoface Selectivity During Phthalimidonitrene Additions to (E)–and(Z)–Configurated α,β–Unsaturated Esters, Induced by a Chiral Center in the γ–Position", *Helvetica Chimica Acta* (1989), 72, pp. 1095–1106.

Cutler et al., "New Antibacterial Agents. 2–Acylamino–1–(4–hydrocarbonylsulfonylphenyl)–1, 3–propanediols and Related Compounds", (Nov. 1952), 74, pp. 5475–5481.

Davis, F.A. et al., "Asymmetric Synthesis of Sulfinimines: Chiral Ammonia Imine Synthons", *Tetrahedron Lett.* (1993) 34:39, pp. 6229–6232.

Davis, F.A. et al., "Asymmetric Synthesis and Reactions of cis–N–(p–Toluenesulfinyl)aziridine–2–Carboxylic Acids", *J. Org. Chem.* (Jun. 1994) 59:12, pp. 3243–3245.

Dubois, L. et al., "Stereocontrolled Synthesis of Aziridine–2–Lactones from D–Ribose and D–Lyxose", (1993) *Tetrahedron* 49:4, pp. 901–910.

Dubois, L. et al., "Preparation of β–Substituted Tryptophan Derivatives: Comparison of the Reactivity of N–Methylindole toward Aziridine–2–lactones and Aziridine–2–carboxylic Esters and Interpretation of Results Using MNDO Calculations", (1994) *J. Org. Chem.* 59:2, pp. 434–441.

Egli, M. et al., "147. Synthese von racemischen Aminozuckersäure–lactonen:xylo–und lyxo–2, 3–Diacetylamino–5–acetoxypentan–4–olid und –2,3, 5–Triacetylaminopentan–4–olid", *Helvetica Chimica Acta* (1986) 69, 1442–1460.

Evans, D.A. et al., "Bis(oxazoline)–Copper Complexes as Chiral Catalysts for the Enantioselective Aziridination of Olefins", *J. Am. Chem. Soc.* (1993) 115:12, pp. 5328–5329.

(List continued on next page.)

*Primary Examiner*—Joseph McKane
*Assistant Examiner*—Dominic Keating
*Attorney, Agent, or Firm*—Panitch Schwarze Jacobs & Nadel, P.C.

[57] ABSTRACT

Novel N-sulfinyl-2-carboxyaziridine compounds and novel N-hydrogen-2-hydroxymethylaziridine compounds are provided. The asymmetric synthesis of N-sulfinylaziridines is readily accomplished in high diastereomeric purity and good yield by the Darzens-type reaction of the metal enolate of an α-haloester and an enantiopure sulfinimine. Ring-opening of these aziridines affords α-amino acids and the otherwise difficult to prepare syn-β-hydroxy-α-amino acids, both key structural units found in many bioactive materials. The N-sulfinyl radical may be selectively removed from the novel aziridine compounds by treatment with acid or base. Alternatively, the N-sulfinyl radical may be oxidized to provide the corresponding N-sulfonyl-aziridine, or reduced to form the corresponding 1H-2-hydroxymethylaziridine, either of which may subsequently be ring-opened to provide precursors to bioactive compounds.

17 Claims, No Drawings

OTHER PUBLICATIONS

Evans, D.A. et al., "Development of the Copper–Catalyzed Olefin Aziridination Reaction", *J. Am. Chem. Soc.* (1994) 116:7, pp. 2742–2753.

Fuji, K. et al., "A New Access to Chiral Aziridines by Enzymatic Transesterification of Meso–Bis(Acetoxymethyl)Aziridines", *Tetrahedron Lett.* (1990) 31:46, pp. 6663–6666.

Fujisawa, T. et al., "Selective Synthesis of Optically Active 3–Haloazetidin–2–ones or Aziridines by the Condensation of Various Metal Enolates of α–Haloacetate with a Chiral Imine", *Tetrahedron* (1992), 47, pp. 7903–7906.

Gelas–Mialhe, Y. et al., "Réactivitédes N–vinylaziridines fonctionnalisées. Synthése. de dérivés des α,β–léhydro α–amino acides", *Can. J. Chem.* (1982) 60, pp. 2830–2851.

Haddach, M. et al., "Synthese et reactivite de Nouveaux Synthons Perfluoroalkyles. Comportement Atypique des Azirines et Aziridines F–Alkylees", *Tetrahedron* (1993) 49:21, pp. 4627–4638.

Hata, Y. et al., "Reaction of Aziridinecarboxylic Acids with Thiols in Aqueous Solution. The Formation of β–Amino Acid", *Tetrahedron* (1987) 43:17, pp. 3881–3888.

Jones, R.J. et al., "Enantiospecific Synthesis of an Aziridinobenzoazocinone, an Advanced Intermediate Containing the Core Nucleus of FR900482 and FK973", *J. Org. Chem.* (1990) 55:4,pp. 1144–146.

Kotera, K. et al., "Conversion of 2–Isoxazolines Into Aziridines by Lithium Aluminum Hydride Reduction", *Tetrahedron* (1970) 26, pp. 539–556.

Kusumoto, S. et al., "Synthesis of Streptolidine (Roseonine, Geamine)", *Bull. Chem. Soc. Jpn.* (1974) 47:11, pp. 2690–2695.

Kuyl–Yeheskiely, E. et al., "One–Step Synthesis of Optically Active Benzyl N–Trityl–L–Aziridine–2–Carboxylic Esters", *Tetrahedron Lett.* (1992) 33, pp. 3013–3016.

Laurent, A. et al., "Thermal Rearrangement of N–Ethoxycarbonylaziridines: A Route to Primary Allylic Amines", *J. Chem. Research.* (S) (1984), pp. 354–355.

Legters, J. et al., "A Convenient Synthesis of Aziridine–2–Carboxylic Esters", *Recl. Trav. Chim. Pays–Bas* (1992), 111:1, pp. 1–5.

Legters, J. et al., "Synthesis of Functionalized Phenylalanine Derivatives by Ring Opening Reactions of 3–Arylaziridine–2–Carboxylic Esters", *Recl. Trav. Chim. Pays–Bas* (1992), 111:1, pp. 16–21.

Li, Z. et al., "Asymmetric Alkene Aziridation with Readily Available Chiral Diimine–Based Catalysts", *J. Am. Chem. Soc.* (1993) 115:12, pp. 5326–5327.

Lown, J.W. et al., "Studies Relating to Aziridine Antitumor Antibiotics. Part I, Asymmetric Syntheses. Part II. Chiral Aziridines and their Conversion to α–Aminoacids", *Can. J. Chem.* (1973) 51, pp. 856–869.

McClure, K.F. et al., "A Remarkable Stereochemical Inversion in Some Heck Arylation Reactions. A Mechanistic Proposal", *J. Org. Chem.* (1994) 59:2, pp. 355–360.

Nakajima, K. et al., "Studies on Aziridine–2–Carboxylic Acid. I. Synthesis of the Optically Active L–Aziridine–2–Carboxylic Acid and its Derivatives", *Bull. Chem. Soc. Jpn.* (1978) 51:5, pp. 1577–1578.

Nakajima, K. et al.,"Studies on 2–Aziridinecarboxylic Acid. III. Reaction of 1–Acyl–2–Aziridinecarboxylic Acid Peptide with Amines", *Bull. Chem. Soc. Jpn.* (1980) 53:1, pp. 283–284.

Nakajima, K. et al., "Studies on 2–Aziridinecarboxylic Acid VI. Synthesis of β–Alkoxy–α–Amino Acids via Ring–Opening Reaction of Aziridine", *Bull. Chem. Soc. Jpn.* (1982) 55:3, pp. 3049–3050.

Nakajima, K. et al., "Studies on 2–Aziridinecarboxylic Acid. IX. Convenient Synthesis of Optically Active S–Alkylcysteine, threo–S–Alkyl–β–Methylcysteine, and Lanthionine Derivatives via the Ring–Opening Reaction of Aziridine by Several Thiols", *Bull. Chem. Soc. Jpn.* (1983) 56:2, pp. 520–522.

Ploux, O. et al., "A New Modified Amino Acid: 2–Amino–3–Mercapto–3–Phenylpropionic Acid (3–Mercaptophenylalanine). Synthesis of Derivatives, Separation of Stereoisomers, and Assignment of Absolute Configuration", *J. Org. Chem.* (1988) 53:14, pp. 3154–3158.

Schumacher, D.P. et al., "An Efficient Synthesis of Florfenicol", *J. Org. Chem* (1990) 55:18, pp. 5291–5294.

Shaw, K.J. et al., "Routes to Mitomycins. Chirospecific synthesis of Aziridinomitosenes", *J. Org. Chem.* (1985) 50:23, pp. 4515–4523.

Shima, I. et al., "Synthesis of Optically Active β–Methyltryptophans From Aziridine–2–Carboxylates", *Chem. Pharm. Bull.* (1990) 38:2, pp. 564–566.

Thijs, L. et al., "Synthesis of all Four Homochiral Stereoisomers of Methyl 3–Phenyl–1H–Aziridine–2–Carboxylate", *Tetrahedron* (1990) 46, pp. 2611–2622.

Tsuge, O. et al., "A Novel Ring–Opening Reaction of Aziridine Induced by the Formation of Nitrogen–Substituted Carbanion of Nonstabilized Type", *Heterocycles* (1984) 22:9, pp. 1955–1958.

Wade, T.N., "Preparation of Fluoro Amines by the Reaction of Aziridines with Fluoride in Pyridine Solution", *J. Org. Chem.* (1980) 45:26, pp. 5328–5333.

Yang, T.K. et al., "Application of New Camphor–Derived Mercapto Chiral Auxillaries to the Synthesis of Optically Active Primary Amines", *J. Org. Chem.* (1994) 59:4, pp. 914–921.

5,789,599

1

AZIRIDINE COMPOUNDS, METHODS OF PREPARATION AND REACTIONS THEREOF

STATEMENT OF GOVERNMENT INTEREST

This invention was made, in part, with Government support awarded by the National Science Foundation and the National Institutes of Health.

FIELD OF THE INVENTION

The invention is directed to heterocyclic organic compounds containing a three-membered hetero ring having two carbons and one nitrogen, and more specifically to racemic and nonracemic 1-sulfinyl-2-carboxyaziridine compounds, 1-sulfinyl-2-(hydroxymethyl)aziridine compounds, stereospecific reactions for their preparation, and conditions for their conversion into components of bioactive compounds.

BACKGROUND OF THE INVENTION

The development of synthetic methodology to prepare biologically active compounds is an important area of chemical research. Given the chiral nature of most biological systems, facile access to optically active compounds is of particular interest.

Unsubstituted N-phenylsulfinylaziridine has been reported in non-optically active form. See, e.g., Anet, F. A. L.; Trepka, R. D.; Cram, D. J. *J. Am. Chem. Soc.* 1967, 89, 357. Methyl 1-(phenylsulfinyl)-2-aziridinecarboxylate has also been reported in non-optically active form. See, e.g., Chervin, I. I.; Fomichev, A. A.; Moskalenko, A. S.; Zaichenko, N. L.; Aliev, A. E.; Prosyanik, A. V.; Voznesenskii, V. N.; Kostyanovskii, R. G. *Izv. Akad. Nauk SSSR, Ser. Khim.* 1988, 1110, *Chem. Abstr.* 1989, 110, 56755g.

Enantiopure α-amino acids, syn- and anti-β-hydroxy-α-amino acids, P-substituted-α-amino acids and their derivatives are essential components of many biologically active peptides, aminosugars and antibiotics, and their preparation is therefore of keen interest to manufacturers of such biologically active materials. See, generally, Sunazuka, T.; Nagamitsu, T.; Tanaka, H.; Omura, S.; Sprengeler, P. A.; Smith III, A. B. *Tetrahedron Lett.* 1993, 34, 4447; Savage, I.; Thomas, E. J. *J. Chem. Soc. Chem. Commun.* 1989, 717; Mukaiyama, T.; Miwa, T.; Nakatsuka, T. *Chem. Lett.* 1982, 145; Evans, D. A.; Weber, A. E. *J. Am. Chem. Soc.* 1986, 108, 6757. An exemplary target of current interest is (-)-N-benzoyl-(2R,3S)-3-phenylisoserine, the C-13 side chain of the remarkable antitumor agent taxol.

Other examples of bioactive materials containing or potentially derived from aziridine 2-carboxylic acids or 1,2-aminoalcohols include the commercially important broad spectrum antibiotics chloramphenicol, thiamphenicol and florfenicol, useful against gram-positive and gram-negative organisms, see, e.g., Tyson, R., *Chem. and Industry* 1988, 118; cromakalim, the smooth muscle relaxant useful for the treatment of asthma and hypertension, see, e.g., Evans, J. M.; Longman, S. D. *Ann. Rep. Med. Chem.* 1991, 26, 73; the diastereoisomers of 3-hydroxyleucine found in naturally occurring peptide antibiotics, see, e.g., Sunazuka, T.; Nagamitsu, T.; Tanaka, H.; Omura, S.; Sprengeler, P. A.; Smith III, A. B. *Tetrahedron Lett.* 1993, 34, 4447; methyl (2R,3R)-1-benzyl-3-hydroxymethyl-2-aziridinecarboxylate, a key intermediate in the synthesis of FK973, active against various transplanted human and murine tumors, see, e.g., Jones, R. J.; Rapoport, H. *J. Org. Chem.* 1990, 55, 1144; and the antitumor mitomycin analogues, see, e.g., Shaw, K. J.; Luly, J. R.; Rapoport, H. *J. Org. Chem.* 1985, 50, 4515.

2

Synthetic methodology for the preparation of nonracemic aziridine compounds outside the scope of the present invention is known. For example, synthetic and naturally occurring β-hydroxy-α-amino acids are reportedly cyclized to form nonracemic aziridine compounds. See, e.g., Jones, R. J.; Rapoport, H. *J. Org. Chem.* 1990, 55, 1144; Kuyl-Yeheskiely, E.; Lodder, M.; van der Marel, G. A.; van Boom, J. H. *Tetrahedron Lett.* 1992, 33, 3013; and Nakajima, K.; Takai, F.; Tanaka, T.; Okawa, K. *Bull. Chem. Soc. Jpn.* 1978, 51, 1577. The viability of this method for the preparation of a diverse range of optically active aziridine compounds is limited by the scarcity of the β-hydroxy-α-amino acid starting materials.

Other methodology has been reported which provides optically active aziridine compounds only after lengthy, multi-step procedures that often require resolutions and/or separation of diastereomers. See, generally, Legters, J.; Thijs, L.; Zwanenburg, B. *Recl. Trav. Chim. Pays-Bas* 1992, 111, 1; and Evans, D. A.; Faul, M. M.; Bilodeau, M. T.; Anderson, B. A.; Barnes, D. M. *J. Am. Chem. Soc.* 1993, 115, 5328. For example, ammonia reportedly reacts diastereoselectively with nonracemic α-bromo-α,β-unsaturated esters to form nonracemic aziridine compounds. See, e.g., Lown, J. W.; Itoh, T.; Ono, N. *Can. J. Chem.* 1973, 51, 856; and Ploux, O.; Caruso, M.; Chassaing, G.; Marquet, A. *J. Org. Chem.* 1988, 53, 3154. Oxirane 2-carboxylic esters may reportedly be converted to aziridines. See, e.g., Thijs, L.; Porskamp, J. J. M.; van Loon, A. A. W. M.; Derks, M. P. W.; Feenstra, R. W.; Legters, J.; Zwanenburg, B. *Tetrahedron* 1990, 46, 2611. The enzymatic transesterification of meso-bis(acetoxymethyl)aziridines has been reported to form nonracemic aziridine compounds. See, e.g., Fuji, K.; Kawabata, T.; Kiryu, Y.; Sugiura, Y.; Taga, T.; Miwa, Y. *Tetrahedron Lett.* 1990, 31, 6663.

The regio- and stereo-selective ring opening reactions of N-activated cis- and trans-2-carboxyaziridines have previously been reported in the preparation of both protogenic and nonprotogenic amino acids. See, e.g., Baldwin, J. E.; Spivey, A. C.; Schonfield, C. J.; Sweeney, J. B. *Tetrahedron* 1993, 49, 6309; Legters, J.; Willems, J. G. H.; Thijs, L.; Zwanenburg, B. *Recl. Trav. Chim. Pays-Bas* 1992, 111, 59; Shima, I.; Shimazaki, N.; Imai, K.; Hemmi, K.; Hashimoto, M. *Chem. Pharm. Bull.* 1990, 38, 564; Hata, Y.; Watanabe, M. *Tetrahedron* 1987, 43, 3881; Nakajima, K.; Oda, H.; Okawa, K. *Bull. Chem. Soc. Jpn.* 1983, 56, 520; Nakajima, K.; Neya, M.; Yamada, S.; Okawa, K. *Bull. Chem. Soc. Jpn.* 1982, 55, 3049; Wade, T. N. *J. Org. Chem.* 1980, 45, 5328; and Williams, R. M. "Synthesis of Optically Active α-Amino Acids." Pergamon Press, New York 1989.

The preparation of N-sulfonylaziridines has proven to be non-trivial according to methods recognized in the art. See, e.g., Legters, J.; Thijs, L.; Zwanenburg, B. *Recl. Trav. Chim. Pays-Bas* 1992, 111, 16.

SUMMARY OF THE INVENTION

One aspect of the invention is a 2-carboxy-1-sulfinylaziridine compound of general formula (I), including the optically active isomers (Ia) or (Ib), and the salts thereof

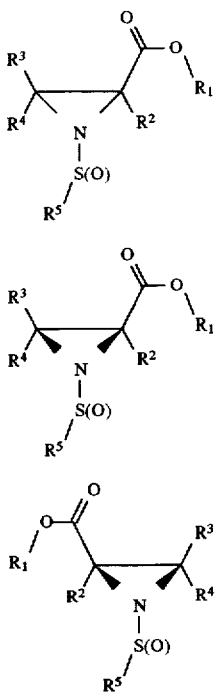

wherein $R^1$, $R^2$, $R^3$, $R^4$ and $R^5$ are independently selected from the group of radicals consisting of hydrogen and hydrocarbon radicals, wherein each of said hydrocarbon radicals independently has from 1 to 40 carbon atoms, 0–40 halogen atoms, and 0–10 heteroatoms selected from the group consisting of boron, nitrogen, oxygen, sulfur, phosphorous, silicon and selenium, with the proviso that $R^3$ and $R^4$ are not simultaneously hydrogen, and S(O) represents a sulfinyl group in either racemic or optically enriched form.

Another aspect of the invention is a process for preparing 2-carboxy-1-sulfinylaziridine compounds of general formula (I), including the isomers (Ia) or (Ib), comprising reacting a compound of formula (II) with base to form a reactive intermediate, and then reacting the reactive intermediate with a compound of formula (III), wherein the compounds of formulas (II) and (III) have the structures,

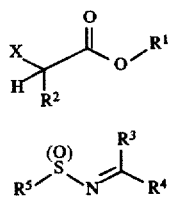

wherein X is a leaving group including halogen and sulfonate esters such as mesylate and tosylate, and $R^1$, $R^2$, $R^3$, $R^4$ and $R^5$ are as defined for compounds of formula (I), and S(O) represents a sulfinyl group in either racemic or optically enriched form.

Another aspect of the invention is a process comprising treating a 2-carboxy-1-sulfinylaziridine compound of general formula (I), including the isomers (Ia) or (Ib), with acid or base. Treatment of a 2-carboxy-1-sulfinyl-aziridine compound of general formula (I), including the optical isomers (Ia) or (Ib), with acid or base, provides the corresponding N-hydrogen aziridine and/or, by ring-opening, a 1,2-aminoalcohol, in a product ratio determined by the reaction conditions. The product(s) are useful precursors to bioactive compounds.

Another aspect of the invention is a process comprising treating a 2-carboxy-1-sulfinylaziridine compound of general formula (I), including the isomers (Ia) or (Ib), with an oxidizing agent. Treatment of a 2-carboxy-1-sulfinylaziridine compound of general formula (I), including the isomers (Ia) or (Ib), with an oxidizing agent, provides the corresponding 2-carboxy-1-sulfonylaziridine compound, where said 2-carboxy-1-sulfonylaziridine compound is a useful precursor to bioactive compounds.

Another aspect of the invention is a process comprising treating a 2-carboxy-1-sulfinylaziridine compound of general formula (I), including the isomers (Ia) or (Ib), with a reducing agent. Treatment of a 2-carboxy-1-sulfinylaziridine compound of general formula (I), including the optical isomers (Ia) or (Ib), with a reducing agent, provides the corresponding 2-hydroxymethyl-1H-aziridine compound, where said 2-hydroxymethyl-1H-aziridine compound is a useful precursor to bioactive compounds.

Another aspect of the invention is a 2-hydroxymethyl-1H-aziridine compound of general formula (VII), including the optical isomers (VIIa) or (VIIb),

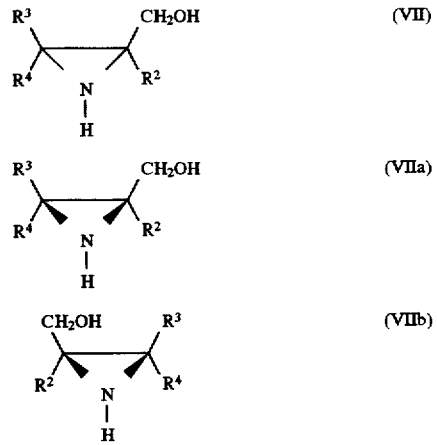

wherein $R^2$, $R^3$ and $R^4$ are independently selected from the group of radicals consisting of hydrogen and hydrocarbon radicals, wherein each of said hydrocarbon radicals independently has from 1 to 40 carbon atoms, 0–40 halogen atoms, and 0–10 heteroatoms selected from the consisting of boron, nitrogen, oxygen, sulfur, phosphorous, silicon and selenium, with the proviso that when $R^2$ is hydrogen, neither $R^3$ nor $R^4$ is hydrogen.

Another aspect of the invention is a method for synthesizing florfenicol, thiamphenicol or chloramphenicol comprising the steps of reacting a 2-carboxy-1-sulfinylaziridine compound of formula (Ia1) with a reducing agent to provide a 2-(hydroxymethyl)aziridine compound of formula (VIIa1), and treating the compound of formula (VIIa1) with acid or base to provide an aminoalcohol compound of formula (VIIIa1), and converting a compound of formula (VIIIa1) to florfenicol, thiamphenicol or chloramphenicol, wherein the compounds of formulas (Ia1), (VIIa1) and (VIIIa1) have the formulas

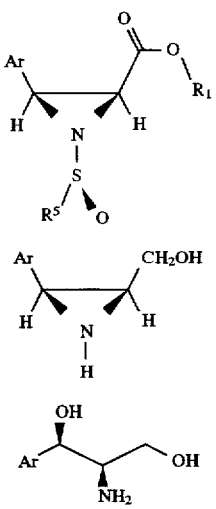

wherein Ar represents para-CH$_3$S(=O)$_2$—C$_6$H$_4$— or a precursor thereof, e.g., para-CH$_3$S(=O)—C$_6$H$_4$— and para-CH$_3$—S—C$_6$H$_4$—, when either florfenicol or thiamphenicol is being synthesized, and Ar represents para-NO$_2$—C$_6$H$_4$— or a precursor thereof when chloramphenicol is being synthesized, and R$^1$ and R$^5$ are as defined for compounds of formula (I).

DETAILED DESCRIPTION OF THE PREFERRED EMBODIMENTS

The present invention is directed to novel 2-carboxy-1-sulfinylaziridine compounds of general formula (I), including the optical isomers (Ia) or (Ib), having substituents R$^1$, R$^2$, R$^3$, R$^4$ and R$^5$. Each of R$^1$, R$^2$, R$^3$, R$^4$ and R$^5$ in compounds of formula (I), collectively referred to herein as the "R" groups of the invention, is independently either hydrogen or a hydrocarbon radical, where the latter is also known as a hydrocarbyl group. The expression hydrocarbon radical is intended to mean a stable atomic grouping held together as a discrete unit by nonionic bonding, where the atomic grouping includes both carbon and hydrogen atoms, and may optionally include one or more boron, nitrogen, oxygen, sulfur, phosphorous, silicon and/or selenium atoms. Each hydrocarbyl group present in the aziridine compound of formula (I) may independently have from 1 to 40 carbon atoms, from 0 to 40 halogen atoms and from 0 to 10 heteroatoms selected from the group consisting of boron, nitrogen, oxygen, sulfur, phosphorous, silicon and selenium.

The expression "nonionic bonding" is intended to include covalent bonding, wherein electrons are shared between two atoms so as to form a bond between the atoms, and where no net charge resides on either of the bonding atoms, as occurs in ionic bonding. The term covalent bonding is intended to include both polar and nonpolar covalent bonding, where polar covalent bonding is present, for example, in a C—F bond where the electrons are not shared equally by the two bonded atoms.

While the bond between a carbon and a hydrogen atom of the hydrocarbyl radicals of the invention will always be a single bond (two shared electrons), the bond between any two carbon atoms may be either a single bond, a double bond (four shared electrons), a triple bond (six shared electrons) or a normalized bond, where normalized bonds are recognized as those bonds that join the carbons of, for example, benzene.

The carbon atoms of a hydrocarbyl group of the invention may be joined together to form acyclic or alicyclic atomic groupings, where the later may be aliphatic or aromatic. Exemplary arrangements of atomic groupings of aliphatic carbon atoms in an acyclic arrangement include methane (C$_1$), ethane (C$_2$), propane (C$_3$), butane (C$_4$), pentane (C$_5$), etc., where for convenience the names are given for the saturated arrangement of carbon atoms only. It should be understood that both straight chain as well as branched atomic arrangements are possible for the "R" groups of the invention. However, it will be again mentioned that the bond between any two carbon atoms in an acyclic arrangement of said carbon atoms may take the form of a single (saturated) bond, or an unsaturated bond such as a double bond or a triple bond, where such atomic groupings are also commonly known as alkyl, alkenyl and alkynyl groups, respectively. Thus, included within, for example, the butane (C$_4$) atomic grouping of carbon atoms according to the invention are the straight-chain fully saturated n-butane group, the straight-chain unsaturated groups 1-butenyl, 2-butenyl, 3-butenyl, 1,3-butadienyl, 1-butynyl, 2-butynyl, 3-butynyl, 1,3-butadiynyl, the branched-chain fully saturated groups sec-butyl, iso-butyl and t-butyl, as well as the branched-chain unsaturated groups 1-methylenepropyl, 1-methyl-1-propenyl, 1-methyl-2-propenyl, 2-methyl-1-propenyl and 2-methyl-2-propenyl. Only stable arrangements of atomic groupings are contemplated for the R groups of the invention.

Exemplary arrangements of atomic groupings of aliphatic and aromatic carbon atoms in an alicyclic arrangement include cyclopropane (C$_3$), cyclobutane (C$_4$), cyclopentane (C$_5$), cyclohexane (C$_6$) etc. where for convenience, the names are given for the saturated monocyclic arrangement of carbon atoms only. Partially or fully unsaturated rings of the indicated carbon number are also included within the scope of the R groups of the invention, as well as polycyclic arrangments. Such monocyclic arrangements are commonly known as cycloalkyl, cycloalkenyl, cycloalkynyl and aryl. Thus, using cyclohexane (C$_6$) as an example, the R groups of the invention include the fully saturated cyclohexyl group, and the partially unsaturated 1-cyclohexenyl, 2-cyclohexenyl, 3-cyclohexenyl, 1,3-cyclohexadienyl, 1,4-cyclohexadienyl, 1,5-cyclohexadienyl, 2,4-cyclohexadienyl and 2,5-cyclohexadienyl groups. In the case of a C-6 ring, the fully unsaturated ring is phenyl, an aromatic ring, which is also included within the scope of the R groups of the invention.

The term polycyclic arrangement refers to two or more rings joined together in a fused, spiro or bridged fashion. Two rings joined together in a fused fashion are distinguished by sharing a bond, as for example, in decalin or a steroid such as cholesterol. Two rings joined together in a spiro fashion are distinguished by sharing a single atom, as for example, in spiropentane. Rings joined together in bridged fashion may be bicyclic, i.e., have two bridgehead atoms, or tricyclic, i.e., have three bridgehead atoms, etc. Adamantyl is an exemplary bridged ring system according to the invention. 1,7,7-Trimethylbicyclo[2.2.1]heptyl is an exemplary alkyl substituted bicyclic bridged ring system according to the invention.

The "R" groups of the invention may contain one or more of the above atomic groupings. Thus, an "R" group may comprise one or more acyclic or alicyclic atomic groupings, which may be aliphatic or aromatic, and which are joined together by nonionic bonding. An example of an "R" group according to the invention having both an aromatic group and a alicyclic group is the toluene radical, also known as tolyl, formed by the nonionic bonding of a phenyl group to a methyl group.

Each "R" group of the invention may optionally and independently contain up to 10 heteroatoms selected from the group consisting of boron, nitrogen, oxygen, sulfur, phosphorous, silicon and selenium. When a heteroatom is present as part of an "R" group of the invention, such heteroatom may be part of the following atomic groups, which are exemplary and not intended to be limiting: acetal, acid chloride, alcohol, aldehyde, alkoxy, alkylthio, arylthio, amide, amine (primary, secondary and tertiary), amino, anhydride, aryloxy, azido, azino, azo, azoxy, boro, carbamido, carbamoyl, carbamyl, carbazoyl, carbonyl, carboxamide, carboxy, carboxylic acid, cyanamido, cyanoto, cyano, cycloalkoxy, diazo, diazoamino, disilanyl, disiloxanoxy, disulfinyl, dissulfide, dithio, ester, ether, formamido, formylamino, formyl, guanadino, guanyl, hydrazino, hydrazo, hydroperoxy, hydroxamino, hydroxy or hydroxyl, imide, imine, imino, iodoso, isocyanato, isocyano, isonitroso, isothiocyanato, isothiocyano, ketal, ketone, lactam, lactone, mercapto, nitramino, nitrile, nitro, nitrosamino, nitrosimino, nitroso, oxamido, oxime, oxo, peroxide, phosphino, phosphinyl, phospho, phosphono, selenyl, silyl, silylene, sulfamino, sulfamyl, sulfeno, sulhydryl, sulfide, sulfinyl, sulfo, sulfonamide, sulfonic acid, sulfonyl, sulfonyl halide, thioacetal, thioaldehyde, thiocarbamyl, thiocarbonyl, thiocarboxy, thiocyanato, thioketal, thiol, thioester, thionyl, ureido, and urethane. Furthermore, any of the aforementioned heteroatom-containing functional groups may be part of an acyclic or alicyclic, aromatic or aliphatic atomic arrangment.

Each "R" group of the invention may independently contain up to 40 halogen atoms, where the halogen atom at each occurrence is independently selected from the group consisting of fluoro, chloro, bromo and iodo. Thus, the "R" groups of the invention may be or may contain the trifluoromethyl, chloromethyl, pentabromophenyl or iodomethyl groups.

When the carbon atoms join together to form one or more rings, one or more of the carbon atoms may be replaced with a heteroatom selected from the group consisting of boron, nitrogen, oxygen, sulfur, phosphorous, silicon and selenium. Examples of nitrogen containing rings include acridine, imidazole, indole, indoline, naphthyridine, piperidine, piperazine, pteridine, pyrazine, pyrazole, pyridine, pyrrole, pyrrolidine, 1,4,7-triazacyclononane, 1,5,9-triazacyclododecane, triazole, triazine, 1H-1,2,3-triazolo[4,5-b]pyridine, 1,2,4-triazolo[1,5-a]pyrimidine, s-triazolo[4,3-a]quinoline and fully or partially saturated derivatives thereof.

Examples of oxygen containing rings include furan, oxirane and tetrahydrofuran Examples of sulfur containing rings include tetrahydrothiophene and thiophene.

Examples of rings containing nitrogen and sulfur include 2,1,3-benzothiadiazole, benzothiazole, phenothiazine, thiazole and fully or partially saturated derivatives thereof. Examples of rings containing nitrogen and oxygen include benzoxazole, morpholine, oxazoline, phenoxazine, and fully or partially saturated derivatives thereof.

The "S(O)" designation present in structural formulas (I), (Ia) or (Ib), or in any other structural formula provided herein, represents a sulfinyl group in either racemic, optically enriched or optically pure form.

Preferred carboxyaziridine compounds of the invention are those of formula (I), (Ia) or (Ib) wherein $R^1$, $R^2$, $R^3$, $R^4$ and $R^5$ are independently selected from the group of radicals consisting of hydrogen and hydrocarbon radicals, wherein each of said hydrocarbon radicals independently has from 1 to 40 carbon atoms, 0–40 halogen atoms, and 0–10 heteroatoms selected from the group consisting of boron, nitrogen, oxygen, sulfur, phosphorous, silicon and selenium, with the proviso that $R^3$ and $R^4$ are not simultaneously hydrogen, and S(O) represents a sulfinyl group in either racemic or optically enriched form. More preferred are compounds of formula (I), (Ia) or (Ib) wherein the hydrocarbon radical having from 1 to 40 carbon atoms is selected from the group consisting of aliphatic radicals, aromatic radicals and combinations thereof, where an aliphatic radical includes acyclic and alicyclic radicals, where the acyclic radical includes straight- and branched-chain acyclic radicals, where the alicyclic radical includes bicyclic and other polycyclic radicals, and where the aliphatic or aromatic radical contains 0–10 heteroatoms and 0–40 halogen atoms.

Preferred compounds of the invention have the formula (I), (Ia) or (Ib) wherein $R^5$ comprises an aromatic radical bonded to the sulfur atom in the —S(O)— group to which $R^5$ is appended. Exemplary $R^5$ groups having an aromatic radical bonded to the sulfur atom in the —S(O)— group include phenyl and substituted phenyl, wherein the substitution on phenyl may take the form of a single methyl group in either the ortho-, meta- or para-positions, so as to provide the tolyl radical, with para-tolyl being especially preferred, or may take the form of two or more methyl groups, so as to provide the xylyl radical, or may take the form of two or more alkyl or alkoxy groups having 2–10 carbon atoms and 0–6 heteroatoms selected from the group consisting of boron, nitrogen, sulfur, oxygen, phosphorous, silicon and selenium, including halogenated derivatives thereof. Additional preferred $R^5$ groups include ortho-, meta- and para-halogenated phenyl, ortho-, meta- and para-nitrophenyl, 1- and 2-naphthyl and 2-, 3-, 4-methoxynaphthyl.

Preferred compounds of the invention have the formula (I), (Ia) or (Ib) wherein each of the "R" groups is independently selected from group consisting of phenyl, naphthyl, bicyclo[2.2.1]heptyl, $C_1$–$C_{10}$ alkyl, $C_1$–$C_{10}$ alkenyl, $C_3$–$C_{10}$ cycloalkyl, oxazolidyl, pyridyl, pyrazyl, cholesteryl and diacetone-D-glucose, wherein any selected member may be substituted with 0–7 substituents selected from the group consisting of halogen, nitro, carbonyl, $C_1$–$C_5$ alkoxy, $C_1$–$C_5$ alkyl, hydroxy, phenyl, naphthyl, $C_1$–$C_5$ alkylthio, $C_1$–$C_5$ alkylsulfonyl and benzyloxy. More preferred compounds additionally have $R^2$ and $R^4$ as hydrogen.

Still more preferred compounds of formula (I), (Ia) or (Ib) are those in which $R^1$ is $C_1$–$C_{10}$ alkyl, $R^3$ is a member selected from the group consisting of phenyl, bicyclo[2.2.1]heptyl, $C_1$–$C_5$ alkyl and $C_1$–$C_5$ alkenyl, and wherein the selected member is substituted with 0–5 substituents selected from the group consisting of $C_1$–$C_5$ alkyl, halogen and nitro.

Other preferred compounds of the invention have the formula (I), (Ia) or (Ib) wherein $R^5$ is an aliphatic radical, such as methyl, ethyl, n-propyl, iso-propyl, n-octyl, benzyl, n-butyl, iso-butyl and tert-butyl. Also included are bicyclic aliphatic radicals bonded to the sulfur atom in the —S(O)— group to which $R^5$ is appended. Exemplary $R^5$ groups having such a bicyclic aliphatic radical may be derived from camphor, including the chiral camphor-derived auxiliary 3-mercapto-2-(benzyloxy)-1,7,7-trimethylbicyclo[2.2.1] heptane.

Still further preferred $R^5$ groups include radicals derived from heterocyclic compounds, such as oxazolidonyl, pyridyl, and pyrazyl. Additional $R^5$ groups are chiral auxiliaries such as cholesteryl, diacetone-D-glucose, and Evans' oxazolidinones, e.g., 4-benzyl-2-oxazolidinone, 4-methyl-5- phenyl-2-oxazolidinone and 4-isopropyl-2-oxazolidinone (Evans, D. A.; Faul, M. M.; Colombo, L.; Bisaha, J. J.; Clardy, J.; Cherry, D. *J. Am. Chem. Soc.* 1992, 114, 5977. Marino, J. P.; Bogdan, S.; Kimura, K. *J. Am. Chem. Soc.* 1992, 114, 5566).

Further preferred compounds of the invention have the formula (I), (Ia) or (Ib) wherein at least one of R², R³ or R⁴ is hydrogen.

Additional preferred compounds are those wherein either R³ or R⁴ is hydrogen and the other of R⁴ or R³ is an aliphatic radical having 1 to 40 carbon atoms optionally containing 0–10 heteroatoms and 0–40 halogen atoms. Still further preferred are compounds which additionally have R² as hydrogen.

Additional further preferred compounds of the invention have the formula (I), (Ia) or (Ib) wherein either R³ or R⁴ is hydrogen and the other of R⁴ or R³ is an aromatic radical optionally substituted with 0–5 C₁–C₈ aliphatic radicals, where the aliphatic radical and aromatic radical can together contain 0–10 heteroatoms and 0–40 halogen atoms. Still further preferred are compounds which additionally have R² as hydrogen.

Yet more preferred compounds according to the invention have the formula (I), (Ia) or (Ib) wherein R¹ is C₁–C₄ aliphatic, R² and R⁴ are hydrogen, R³ is selected from the group of radicals consisting of C₁–C₅ aliphatic, C₆ aromatic and combinations thereof containing 0–3 heteroatoms, including alkyl-substituted aryls, and R⁵ is C₆ aromatic substituted with 0–2 C₁–C₃ aliphatic, including tolyl.

Compounds of formula (I) having both R³ and R⁴ as hydrogen are not included among the compounds of the invention. Compounds of formula (I) having both R³ and R⁴ as hydrogen are non-chiral at the 3-position of the aziridine ring, and will ring open under the reaction conditions of the invention to afford a non-chiral carbon atom β to the carboxy radical.

Included within the scope of the inventive carboxyaziridine compounds of formula (I) are the salts thereof, including the aziridinium salts formed by treatment of a compound of formula (I), (Ia) or (Ib) with a protic acid, such as hydrochloric acid and the like.

Compounds of formula (I) can be prepared according to the method outlined in Scheme 1. A compound of formula (II), e.g., methyl α-bromoacetate, is reacted with strong base, e.g., lithium bis(trimethylsilyl)amide, to form a reactive intermediate (R.I.), e.g., the lithium enolate of the compound of formula (II). The reactive intermediate is reacted with a compound of formula (III), e.g., (S)-(+)-N-benzylidene-p-toluenesulfinimine, whereupon a compound of formula (I), e.g., (2S,3S)-(+)-N-p-toluenesulfinyl-2-carbomethoxy-3-phenylaziridine, is formed.

Scheme 1

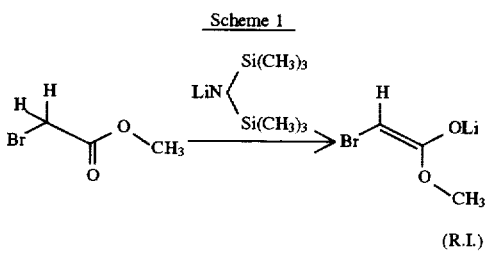

(R.I.)

-continued
Scheme 1

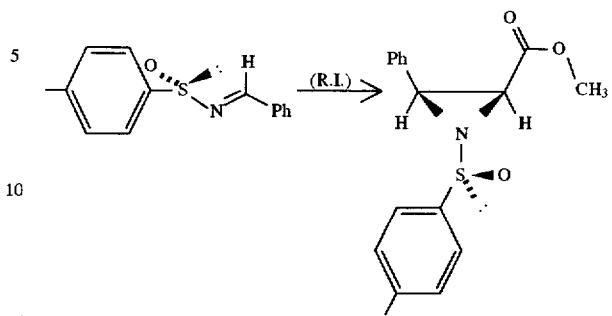

More generally, compounds of formulas (II) and (III) have the structural formulas,

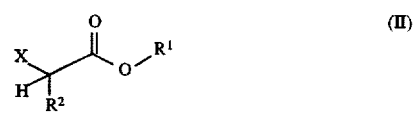
(II)

(III)

wherein X is a leaving group, for example halogen or a sulfonate ester such as mesylate or tosylate, and R¹, R², R³, R⁴ and R⁵ are as defined for compounds of formula (I) and S(O) represents a sulfinyl group in either racemic or optically enriched form. Compounds of formulas (I) and (III) according to this aspect of the invention may simultaneously have R³ and R⁴ equal to hydrogen.

Preferred compounds of formula (III) have an enantiomerically enriched sulfinyl (—S(O)—) group. See, e.g., Davis, F. A.; Reddy, R. E.; Szewczyk, J. M.; Portonovo, P. S. *Tetrahedron Lett.* 1993, 34, 6229; Yang, T. K.; Chen, R. Y.; Lee, D. S.; Peng, W. S.; Jiang, Y. Z.; Mi, A. Q.; Jong, T. T. *J. Org. Chem.* 1994, 59, 914; and references cited therein for the preparation of such enantiomerically enriched compounds. Preferred compounds of formula (III) are represented by structural formulas (IIIa) or formula (IIIb)

(IIIa)

(IIIb)18

The strong base of Scheme 1 is selected from the group of strong bases capable of converting an α-(leaving group) carboxylic ester of formula (II) to the corresponding enolate. Preferred strong bases include lithium, sodium or potassium hydride; lithium, sodium or potassium salts of primary, secondary or tertiary amines such as diisopropylamine and bis(trimethylsilyl)amine; sodium amide; lithium alkyls such as n-butyllithium and methyllithium; and metal salts of organic alcohols such as potassium tert-butoxide and sodium ethoxide. Strong bases according to the invention illustrated by Scheme 1 are typically commercially available, from for example, Aldrich Chemical Company, Inc., Milwaukee, Wisc. Alternatively, a preferred strong base can be prepared by, for example, treating diisopropylamine with n-butyllithium.

The preparation of compounds of formula (I) according to Scheme 1 is preferably conducted in an inert solvent, under an inert atmosphere, and at low temperature. Exemplary inert solvents include, without limitation, 1,4-dioxane, 1,3-dioxolane, diethyl ether, dimethoxyethane, 2-methoxyethylether and tetrahydrofuran. Exemplary inert atmospheres include, without limitation, atmospheres of dry nitrogen or dry argon. Low temperatures according to the invention illustrated by Scheme 1 include temperatures of about −78° C. to about 0° C. In general, the reaction conditions are chosen so as to provide the desired enolate geometry, which will be either the "E" or "Z" geometry. Methods to affirmatively achieve either an "E" or "Z" enolate geometry, starting from α-(leaving group)esters of formula (II), have recently become well-known in the art.

The compounds of formula (II) and (III) are preferably contacted together in a molar ratio of about 2:1 in order to form the aziridine compounds of formula (I) according to Scheme 1. The compound of formula (II) is preferably present in excess because typically it is relatively inexpensive, and the reaction conditions are chosen so as to optimize the incorporation of a compound of formula (III) into an aziridine compound of formula (I). In instances where the compound of formula (II) is more precious, the reaction conditions comprise an excess molar equivalent of the compound of formula (III). In practice, a wide range of molar ratios can be employed, including ratios of less than 0.1:1 to greater than 10:1, where the ratio refers to the moles of formula (II) compound to moles of formula (III) compound, respectively.

After the compound of formula (I) has been prepared as illustrated in Scheme 1, it may be isolated according to methods well-known in the art. For example, the reaction mixture may be quenched by the addition of water. The solvent(s) may then be removed by distillation. The compound of formula (I) may be obtained in purified form by elution through silica gel, e.g., by flash chromatography or high pressure liquid chromatography.

The preparation of the aziridine compounds of formula (I) according to the method illustrated by Scheme 1 is particularly advantageous because of the ease with which aziridine compounds of formula (I) can be prepared with high diastereomeric excesses. This highly desirable result is primarily the consequence of two factors. First, the sulfinimines of formula (III) having exclusively, or nearly exclusively, either the (S) or (R) configuration at the sulfinimine sulfur are available according to known methodology. See, e.g., Davis, F. A.; Reddy, R. E.; Szewczyk, J. M.; Portonovo, P. S. *Tetrahedron Lett.* 1993, 34, 6229 and Yang, T. K.; Chen, R. Y.; Lee, D. S.; Peng, W. S.; Jiang, Y. Z.; Mi, A. Q.; Jong, T. T. *J. Org. Chem.* 1994, 59, 914. Second, the aziridine-forming reaction has been discovered to proceed with high diastereoselectivity, so that the sterically-bulkier radical between $R^3$ and $R^4$ is generally found exclusively in the syn-position relative to the carboxy radical of the aziridine ring when formed. Therefore, by judiciously choosing the desired antipode of the formula (III) compound and the substitution pattern of the formula (II) compound, an aziridine compound of formula (I) can be obtained not only in high yield but also in high diastereomeric excess. The reaction of Scheme 1 can be used to prepare aziridine compounds from both enolizable and nonenolizable sulfinimines. The reaction of Scheme 1 is particularly preferred for the preparation of cis-N-(p-toluenesulfinyl)-2-carbomethoxyaziridines: when either $R^3$ or $R^4$ is hydrogen, the cis-aziridine forms almost exclusively.

Another aspect of the invention comprises the reaction of compounds of formula (I) with acid or base. The compounds of formulas (I), (Ia) and (Ib) according to this aspect of the invention applies to compounds including those wherein $R^3$ and $R^4$ are simultaneously hydrogen. As illustrated in Scheme 2, treatment of compounds of formula (Ia), e.g., (2S,3S)-(+)-N-(p-toluenesulfinyl)-2-carbomethoxy-3-phenylaziridine, with acid or base, e.g., trifluoroacetic acid, can provide an N-hydrogen aziridine compound of formula (Va), e.g., methyl (2S,3S)-(+)-3-phenyl-1H-aziridine-2-carboxylate, or a ring-opened β-hydroxy-α-amino acid compound of formula (IVa), e.g., methyl (2S, 3R)-(+)-2-amino-3-hydroxy-3-phenylpropionate.

Scheme 2

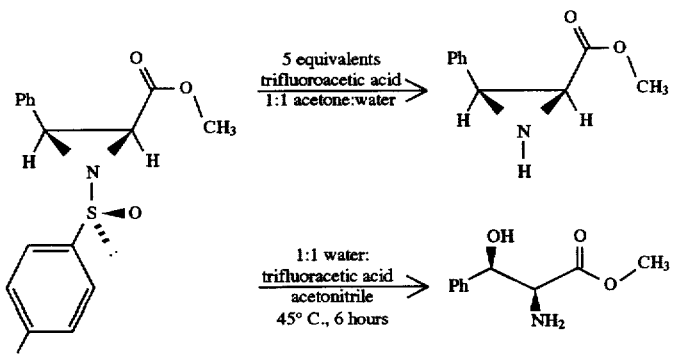

In more general terms, compounds of formula (I) will react with acid or base to provide compounds of formula (IV) and/or (V), while the optical isomers of the compound of formula (I), i.e., compounds of formulas (Ia) or (Ib), will react with acid or base to provide the optically active ring opened compounds of formula (IVa) or (IVb), respectively, or the 1H-aziridine derivatives of formula (Va) or (Vb), respectively, where compounds of formula (IV), (IVa), (IVb), (V), (Va) and (Vb) are represented by the structural formulas:

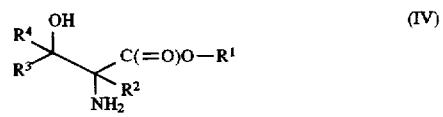

-continued

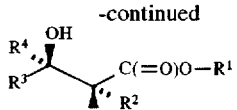
(IVa)

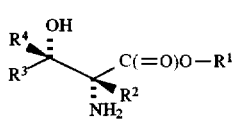
(IVb)

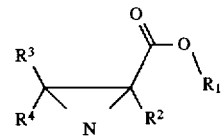
(V)

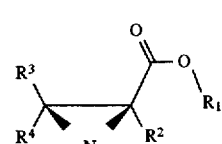
(Va)

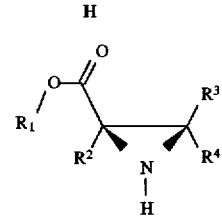
(Vb)

Depending on the reaction conditions chosen, the hydroxyl group of the amino group of the compounds of formula (IV), (IVa) or (IVb) may be converted in situ to a halogen or an ester, in the case of the hydroxyl group, or to a substituted amine.

Exemplary acids include, without limitation, trifluoroacetic acid, hydrochloric acid, sulfuric acid, formic acid, acetic acid, $C_1$–$C_{10}$ alkyl- and alkylaryl-sulfonic acids such as methanesulfonic and camphorsulfonic acid, $C_6$–$C_{15}$ aryl- and arylalkyl-sulfonic acids such as para-toluenesulfonic acid, and acidic ion exchange resins such as Amberlite® IR-120(plus). Exemplary bases include, without limitation, lithium hydroxide, sodium hydroxide, potassium hydroxide, ammonium hydroxide, amines including primary, secondary and tertiary amines, tetrabutylammonium hydroxide, and basic ion exchange resins such as Amberlite® IR-400(Cl).

The enantioselective reactions illustrated in Scheme 2 may be conducted under a wide range of reaction conditions. The reactions may or may not be run under an inert atmosphere of nitrogen or argon. The reaction temperature can range from below room temperature, for example 0° C., to above room temperature, for example, 70° C. The reaction is preferably run in an appropriate solvent, where exemplary solvents include, without limitation, acetonitrile, acetone, water and mixtures thereof.

Whether the ring-opened compound or the N-hydrogen aziridine compound predominates upon treatment of a compound of formula (I) with acid or base depends on a number of factors. Those factors include the amount and identity of the acid or base, the solvent(s) in which the reaction is conducted, the temperature of the reaction and the identity of the compound of formula (I). It is generally observed that ring-opened β-hydroxy-α-amino acid compounds are favored when the reaction is run with about 50% aqueous trifluoroacetic acid in acetonitrile at a temperature of about 45° C. The conversion of a compound of formula (I) to the corresponding N-hydrogen aziridine is generally favored under milder condition, e.g., with reaction conditions comprising 5 moles of trifluoroacetic acid (based on moles of the compound of formula (I)) in a solvent consisting of acetone and water (1:1 volume to volume ratio) and at a temperature of about room temperature (i.e., ca. 25° C.) or slightly higher or lower than room temperature.

Yet another aspect of the invention provides a process comprising treating a compound of formula (I), or a non-racemic isomer (Ia) or (Ib), with an oxidizing agent, where a preferred oxidizing agent is meta-chloroperoxybenzoic acid. As shown in Scheme 3, treatment of a compound of formula (I), e.g., (2S,3S)-(+)-N-(p-toluenesulfinyl)-2-carbomethoxy-3-phenylaziridine, with an oxidizing agent, e.g., meta-chloroperoxybenzoic acid, provides the corresponding sulfonyl compound of formula (VI), e.g., (2S,3S)-(+)-N-(p-toluenesulfonyl)-2-carbomethoxy-3-phenylaziridine.

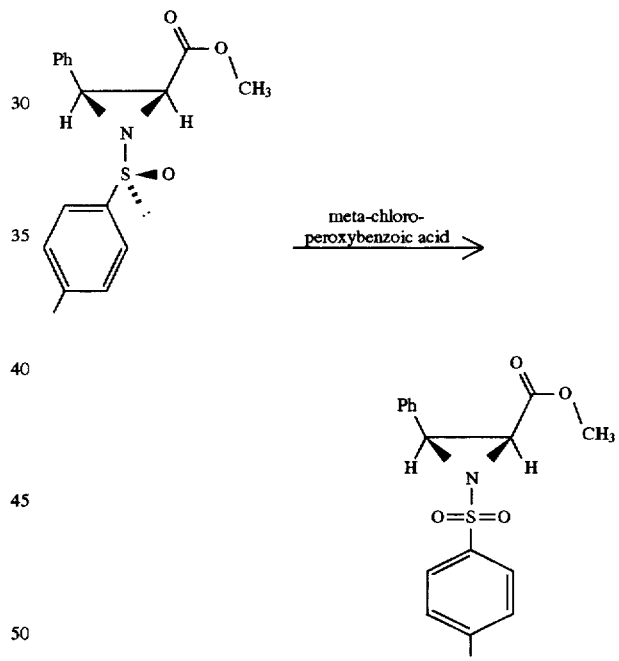

Scheme 3

More generally, the oxidation products of formula (VI), including the optically enriched isomers of formulas (VIa) and (VIb) have the formulas, (VI)

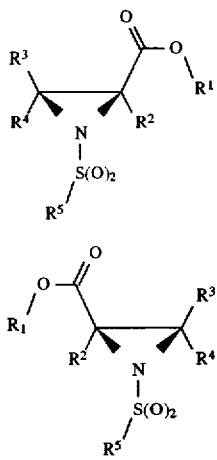

(VIa)

(VIb)

wherein the "R" groups are as defined for compounds of formula (I), and $R^3$ and $R^4$ may simultaneously be hydrogen.

As illustrated by the reaction of Scheme 3, treating a sulfinyl compound of formula (I) with an oxidizing agent converts the sulfinyl radical to a sulfonyl radical. The reaction illustrated by Scheme 3 is a particularly advantageous approach to preparing N-sulfonated aziridine compounds, e.g., N-tosylated aziridine compounds. Such sulfonyl compounds are difficult to prepare by other known synthetic methodology, and provide ready access to α-amino acids and syn-β-hydroxy-α-amino acids, both valued precursors to bioactive compounds. The sulfonated aziridine compounds may undergo ring-opening reactions upon treatment with, e.g., formic acid or trifluoroacetic acid.

Oxidizing agents capable of converting a sulfoxide to a sulfone are preferred in the instant invention. Exemplary oxidizing agents and conditions include, without limitation, meta-chloroperoxybenzoic acid, hydrogen peroxide, peroxyacetic acid, monoperoxyphthalic acid, magnesium salt hydrate, selenium dioxide-hydrogen peroxide, potassium peroxymonopersulfate, chromic acid, potassium permanganate, sodium periodate with catalytic potassium permanganate, tert-butylhypochlorite and N-sulfonyloxaziridine.

The oxidation reaction according to the invention and as illustrated in Scheme 3 may be conducted under a wide range of reaction conditions. The reactions may or may not be run under an inert atmosphere of nitrogen or argon. The reaction temperature can range from below room temperature, for example 0° C., to above room temperature, for example, 70° C. The reaction is preferably run in an appropriate solvent, where exemplary solvents include, without limitation, chloroform, methylene chloride, benzene, toluene, acetic acid and mixtures thereof. The ratio of the moles of oxidizing agent to the moles of formula (I) compound can vary over a wide range, and will depend on the identity of the oxidizing agent. In the case where the oxidizing agent is meta-chloroperoxybenzoic acid, a 50% molar excess of oxidizing agent is satisfactory. The oxidation of organic compounds is well-known in the art, and the skilled artisan will be able to determine satisfactory conditions for the oxidation of the sulfinyl compounds of the invention.

Yet another aspect of the invention provides a process comprising treating a compound of formula (I) or a nonracemic isomer of formula (Ia) or (Ib), with a reducing agent, where a preferred reducing agent is lithium aluminum hydride. As shown in Scheme 4, treatment of a compound of formula (I), e.g., (2S,3S)-N-(p-toluenesulfinyl)-2-carbomethoxy-3-(4-methylthiophenyl)aziridine, with lithium aluminum hydride provides the corresponding 1H-2-(hydroxymethyl)aziridine compound, e.g., (2S,3S)-2-hydroxymethyl-3-(4-methylthiophenyl)-1H-aziridine. This reduction reaction according to the invention is useful in the preparation of bioactive compounds, e.g., florfenicol, thiamphenicol and chloramphenicol, as discussed below.

Scheme 4

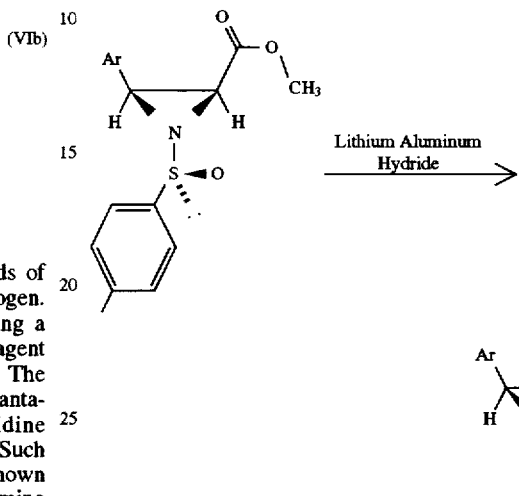

Ar = 4-methylthiophenyl

More generally, the reduction products of formula (VII), including the optically active isomers of formula (VIIa) and (VIIb) have the formulas

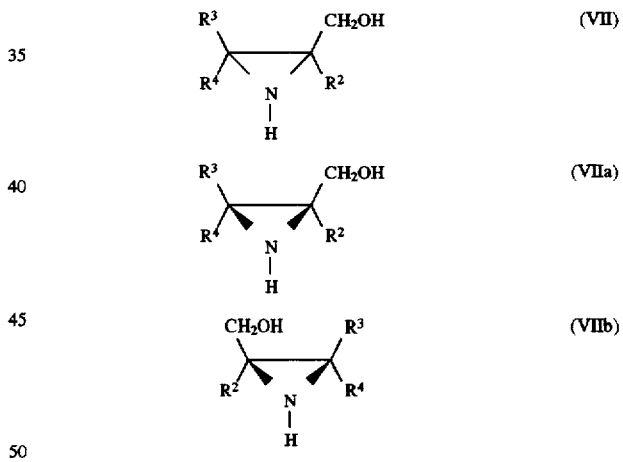

wherein $R^2$, $R^3$ and $R^4$ are as defined previously with regard to compounds of formula (I), although compounds wherein $R^3$ and $R^4$ are simultaneously hydrogen may be prepared according to the inventive method, starting from compounds of formula (I), (Ia) and (Ib) wherein $R^3$ and $R^4$ are simultaneously hydrogen.

The reduction illustrated in Scheme 4 can be conducted under a wide range of reaction conditions. For example, suitable reducing agents include, without limitation, lithium aluminum hydride, sodium borohydride, lithium borohydride, diisobutylaluminum hydride, sodium cyanoborohydride, sodium bis(2-methoxyethoxy)aluminum hydride, calcium borohydride, lithium tri-tert-butoxy hydride, diborane, reducing metal solutions such as lithium/sodium, and hydrogenation techniques. The temperature, solvent(s), atmosphere etc. will need to be tailored to the reducing agent selected, as is well-known to those skilled in the art.

Another aspect of the invention is a 2-hydroxymethyl-1H-aziridine compound of general formula (VII), including the isomers (VIIa) or (VIIb)

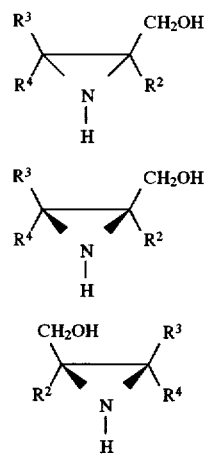

wherein $R^2$, $R^3$ and $R^4$ are as defined previously with regard to compounds of formula (I), with the proviso that when $R^2$ is hydrogen, neither $R^3$ nor $R^4$ is hydrogen.

Preferred compounds of formula (VII) are those wherein the hydrocarbon radical having from 1 to 40 carbon atoms is selected from the group of radicals consisting of aliphatic radicals, aromatic radicals and combinations thereof, where an aliphatic radical includes acyclic and alicyclic radicals, where the acyclic radical includes straight- and branched-chain acyclic radicals, where the alicyclic radical includes bicyclic and other polycyclic radicals; and where the aliphatic or aromatic radical contains 0–10 heteroatoms and 0–40 halogen atoms.

More preferred compounds of formula (VII), (VIIa) or (VIIb) are those wherein $R^2$ is hydrogen.

Additional preferred compounds of formula (VII), (VIIa) or (VIIb) are those wherein at least one of $R^3$ or $R^4$ is an aliphatic radical having 1 to 40 carbon atoms optionally containing 0–10 heteroatoms and 0–40 halogen atoms. Still further preferred are compounds which additionally have $R^2$ as hydrogen.

Additional further preferred compounds of formula (VII), (VIIa) or (VIIb) are those wherein at least one or $R^3$ or $R^4$ is an aromatic radical optionally substituted with 0–5 $C_1$–$C_8$ aliphatic radicals, where the aliphatic radical and aromatic radical can together contain 0–10 heteroatoms and 0–40 halogen atoms. Still further preferred are compounds which additionally have $R^2$ as hydrogen.

Another aspect of the invention is the application of the inventive compounds and synthetic methodology disclosed herein to the preparation of the broad spectrum antibiotics florfenicol, thiamphenicol and chloramphenicol. A previously known synthetic route to these antibiotics entails an undesirable and wasteful resolution of a racemic mixture. See, Schumacher, D. P.; Clark, J. E.; Murphy, B. L. Fischer, P. A. *J. Org. Chem.* 1990, 55, 5291. In contrast, the synthetic route of the present invention begins with an enantiomerically pure aziridine compound of the invention to provide florfenicol, thiamphenicol or chloramphenicol without a resolution step.

Scheme 5

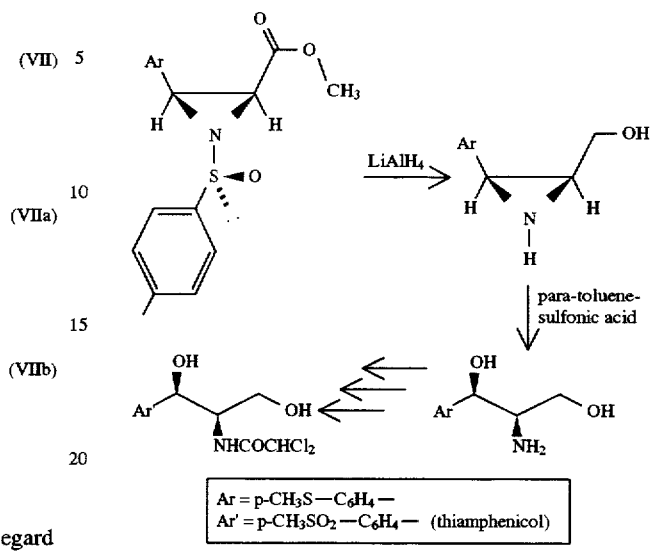

As illustrated in Scheme 5 for the preparation of thiamphenicol, (2S,3S)-N-(p-toluenesulfinyl)-2-carbomethoxy-3-(4-methylthiophenyl)aziridine can be reduced with lithium aluminum hydride to form (2S,3S)-2-methylalcohol-3-(4-methylthiophenyl)-1H-aziridine, which in turn can be treated with acid, such as para-toluenesulfonic acid, to provide the ring-opened compound (2R,3R)-2-amino-1-(4-methylthiophenyl)-1,3-propanediol. The ring-opened compound can be converted to thiamphenicol by synthetic methodology disclosed herein, or can be converted to florfenicol after substitution of the primary hydroxyl group with a fluorine atom.

While the preparation of thiamphenicol as illustrated in Scheme 5 begins with a N-(p-toluenesulfinyl)-2-carbomethoxy aziridine compound, it will be recognized by one skilled in the art that esters other than the methyl ester, and sulfinyl radicals other than p-toluenesulfinyl, may be employed. Any "R" group as defined for compounds of formula (I) may replace one or both of the methyl or p-tolyl groups in the synthesis of thiamphenicol, florfenicol or thiamphenicol according to the method of Scheme 5.

The preparation of chloramphenicol may be achieved by synthetic methodology analogous to that shown in Scheme 5, but the starting 1-sulfinylaziridine preferably has a para-nitrophenyl group, or a precursor thereof, instead of the para-methylthiophenyl group, and the reduction is accomplished with a milder reducing agent, e.g., diborane, so as to preserve the nitro group.

The following examples are provided to better disclose and teach the preparation and reactions of the aziridine compounds of the present invention. They are for illustrative purposes only, and it must be acknowledged that minor variations and changes can be made without materially affecting the spirit and scope of the invention as recited in the claims that follow.

EXAMPLES

General Background. IR spectra were recorded on a Perkin-Elmer 1600 FTIR spectrometer using sodium chloride plates for liquids and potassium bromide disks for solids. $^1$H NMR and $^{13}$C NMR spectra were recorded in $CDCl_3$ solution (unless a different solvent is specified) and referenced to TMS (0.00 ppm) using a Bruker 250 MHz spectrometer. Column chromatography was performed using silica gel, Merck grade 60 (230–400 mesh) purchased from Aldrich Chemical Company. Analytical and preparative thin layer chromatography was performed on pre-coated silica gel plates (250 and 1000 microns) purchased from Analtech Inc. TLC plates were visualized with UV light and/or in an iodine chamber unless noted otherwise. Melting points were recorded on a Mel-Temp™ apparatus and are uncorrected. Optical rotations were measured on a Perkin-Elmer 241 polarimeter. THF was freshly distilled under nitrogen from a purple solution of sodium and benzophenone. Lithium diisopropylamide, 1M solution in THF, was prepared just prior to its by the addition of 4.0 mL (10.0 mmol) n-butyllithium (2.5M solution in hexanes) to a cooled solution of diisopropylamine (1.47 mL, 10.5 mmol) in THF (5.0 mL) at 0° C. and stirring for 20 min.

The sulfinimine compounds used as starting materials in some of the following experimental descriptions were prepared according to F. A. Davis; R. E. Reddy; J. M. Szewczyk; P. S. Portonovo *Tetrahedron Lett.* 1993, 34, 6229; or F. A. Davis; R. T. Reddy; R. E. Reddy *J. Org. Chem.* 1992, 57, 6387.

Example 1

(2S,3S)-(+)-N-(p-Toluenesulfinyl)-2-carbomethoxy-3-phenylaziridine

Into a 50-mL oven-dried two-necked round-bottomed flask equipped with a magnetic stir bar, rubber septum, and argon filled balloon were placed 2.0 mL of 1M lithium bis(trimethylsilyl)amide (in THF) and 10 mL THF. The solution was cooled to −78° C., and 0.306 g (2 mmol) methyl α-bromoacetate added via syringe. After stirring for 30 min. at −78° C., a pre-cooled solution (−78° C.) of 0.243 g (1.0 mmol) of (S)-(+)-N-benzylidene-p-toluenesulfinimine in 10 mL THF was added via cannula over 30 min. The reaction mixture was stirred for 2.5 h at −78° C., quenched at this temperature with 15 mL H₂O, and diluted with 60 mL ethyl acetate. The solution was washed with 10 mL brine, dried (MgSO₄), filtered and concentrated in vacuo to give a residue containing the titled aziridine. The residue was subjected to flash chromatography (ethyl acetate:n-hexane, 2:8) to give the titled compound (0.205 g, 65%) as an oil: $R_f$ 0.45 (ethyl acetate:n-hexane 2:8); $[\alpha]_D^{20}$+51.4° (c 1.5, CHCl₃); IR (neat): 3031.4, 1754.1, 1596.3, 1204.3, 1074.1 cm⁻¹; ¹H NMR (CDCl₃) δ2.43 (s, 3H, CH₃), 3.39 (s, 3H, CH₃), 3.50 (d, J=7.4 Hz, 1H, CH), 3.88 (d, J=7.4 Hz, 1H, CH), 7.20–7.50 (m, 7H, aromatic), 7.72 (d, J=8.2 Hz, 2H, aromatic); ¹³C NMR (CDCl₃) δ165.8, 141.9, 140.6, 132.3, 129.5, 128.1, 127.9, 127.6, 125.0, 51.9, 42.1, 34.8, 21.5. Anal. Calcd for C₁₇H₁₇NO₃S: C, 64.74; H, 5.43. Found: C, 64.72; H, 5.50.

Also isolated was (2S,3R)-(−)-N-(p-toluenesulfinyl)-2-carbomethoxy-3-phenylaziridine (in 6% yield, as a 1:1 syn:anti isomeric mixture with respect to the carbomethoxy group), which was characterized after oxidation to the sulfonyl compound: $R_f$ 0.2, (ethyl acetate:n-hexane 2:8); mp 42°–44° C., (mp 44.2°–44.6° C. according to Evans, D. A. et al. *J. Am. Chem. Soc.* 1993, 115, 5328); $[\alpha]_D^{20}$ −29.4° (c 0.92, CH₂Cl₂); ($[\alpha]_D^{20}$ +33.1° (c 1.0, CH₂Cl₂) for the (2R,3S)-isomer according to Evans, D. A. et al. *J. Am. Chem. Soc.* 1993, 115, 5328).

Example 2

(2R,3R)-(−)-N-(p-Toluenesulfinyl)-2-carbomethoxy-3-phenylaziridine

Following the procedure of Example 1, but substituting (R)-(−)-(benzylidene)-p-toluenesulfinimine (prepared according to Davis, F. A. et al. *Tet. Lett.* 1993, 34, 6229) for (S)-(+)-(benzylidene)-p-toluenesulfinimine, provided the titled aziridine compound (0.220 g, 70%) as an oil: $[\alpha]_D^{20}$ −50.8° (c 1.5, CHCl₃), having spectral properties identical to those of the titled compound of Example 1.

Example 3

(2S,3S)-(+)-N-(p-Toluenesulfinyl)-2-carbomethoxy-3-(4-methoxyphenyl)aziridine

Following the procedure of Example 1, but substituting (S)-(+)-(4-methoxybenzylidene)-p-toluenesulfinimine for (S)-(+)-(benzylidene)-p-toluenesulfinimine, and conducting the flash chromatography with ethyl acetate:n-pentane (ratio 3:7) as the eluent provided the titled compound (74%) as an oil: $[\alpha]_D^{20}$ +26.4° (c 1.7, CHCl₃); IR (neat): 3001.3, 1751.7, 1596.2, 1203.6, 1073.6 cm⁻¹; ¹H NMR (CDCl₃) δ2.25 (s, 3H), 3.23 (s, 3H), 3.28 (d, J=7.3 Hz, 1H), 3.62 (s, 3H), 3.66 (d, J=7.3 Hz, 1H), 6.69 (d, J=8.8 Hz, 2H), 7.16 (d, J=8.2 Hz, 2H), 7.22 (d, J=8.8 Hz, 2H), 7.54 (d, J=8.2 Hz, 2H); ¹³C NMR (CDCl₃) δ166.0, 159.4, 142.0, 140.6, 129.6, 128.9, 125.1, 124.4, 113.5, 55.2, 52.1, 42.0, 34.9, 21.6. Anal. Calcd for C₁₈H₁₉NO₄S: C, 62.59; H, 5.54. Found: C, 62.48; H, 5.28.

Example 4

(2S,3S)-(+)-N-(p-Toluenesulfinyl)-2-carbomethoxy-3-isopropylaziridine

Following the procedure of Example 1, but substituting (S)-(+)-N-isobutylidene-p-toluenesulfinimine (prepared according to Davis F. A. et al. *Tetrahedron Lett.* 1993, 34, 6229 and characterized below) for (S)-(+)-N-benzylidene-p-toluenesulfinimine, and conducting the flash chromatography with ethyl acetate:n-pentane (ratio 1:9) as the eluent provided the titled compound (64%) as an oil: $[\alpha]_D^{20}$ +110.7° (c 1.2, CHCl₃); IR (neat): 2963.6, 1751.9, 1596.9, 1202.7, 1074.2 cm⁻¹; ¹H NMR (CDCl₃) δ0.93 (d, J=6.6 Hz, 3H), 1.17 (d, J=6.6 Hz, 3H), 1.71–1.89 (m 1H), 2.40 (s, 3H), 2.49 (dd, J₁=7.4 Hz, J₂=9.8 Hz, 1H), 3.21 (d, J=7.3 Hz, 1H), 3.61 (s, 3H), 7.29 (d, J=8.1 Hz, 2H), 7.62 (d, J=8.1 Hz, 2H); ¹³C NMR (CDCl₃) δ167.2, 141.5, 140.9, 129.2, 124.5 51.8, 47.4, 31.6, 26.7, 21.2, 20.4, 19.1. Anal. Calcd for C₁₄H₁₉NO₃S: C, 59.76; H, 6.81. Found: C, 59.77; H, 6.95.

The (S)-(+)-N-isobutylidine-p-toluenesulfinimine was purified by flash chromatography (ethyl acetate:hexane, 2:8) to afford an oil: $[\alpha]_D^{20}$ +387.5° (c 2.1, CHCl₃); IR (neat): 2956.1, 1731.9, 1618.5, 1096.1 cm⁻¹; ¹H NMR (CDCl₃) δ0.98 (d, J=2.9 Hz, 3H), 1.01 (d, J=2.8 Hz, 3H), 2.45 (s, 3H), 2.46–2.58 (m, 1H), 7.15 (d, J=8.1 Hz, 2H), 7.40 (d, J=8.2 Hz, 2H,), 7.98 (d, J=4.6 Hz, 1H); ¹³C NMR (CDCl₃) δ170.9, 141.8, 141.3, 129.5, 124.4, 34.6, 21.4, 18.7. Anal. Calcd for C₁₁H₁₅NOS: C, 63.12; H, 7.22. Found: C, 62.96; H, 7.23.

Example 5

(2S,3S)-(+)-N-(p-Toluenesulfinyl)-2-carbomethoxy-3-((2-phenyl)-(E)-1-ethenyl)aziridine Following the procedure of Example 1, but substituting (S)-(+)-N-(3-phenyl-(E)-2-propenylidene)-p-toluenesulfinimine (prepared according to Davis F. A. et al. *Tetrahedron Lett.* 1993, 34, 6229) for (S)-(+)-N-benzylidene-p-toluenesulfinimine, and conducting the flash chromatography with ethyl acetate:n-pentane (ratio 3:7) provided the titled compound (79%): mp 107°–109° C.; $[\alpha]_D^{20}$ +107.3° (c 4.0, CHCl₃); IR (KBr): 1735.2, 1593.9, 1209.7, 1094.9, 1074.0 cm$^{-1}$; $^1$H NMR (CHCl$_3$) δ2.42 (s, 3H), 3.39–3.50 (m, 2H), 3.61 (s, 3H), 6.23 (dd, J$_1$=8.3 Hz, J$_2$=16.0 Hz, 1H), 6.85 (d, J=16.0 Hz, 1H), 7.25–7.42 (m, 7H), 7.64 (d, J=8.1 Hz, 2H); $^{13}$C NMR (CDCl$_3$) δ166.9, 142.0, 140.5, 136.4, 135.6, 129.5, 128.4, 128.1, 126.4, 124.6, 121.2, 52.3, 42.6, 32.7, 21.5. Anal. Calcd for C$_{19}$H$_{19}$NO$_3$S: C, 66.83; H, 5.61. Found: C, 66.38; H, 5.65.

Example 6

(2S,3S)-(+)-N-(p-Toluenesulfinyl)-2-carbomethoxy-3-((1-methyl)-1-propenyl)aziridine Following the procedure of Example 1, but substituting (S)-(+)-N-(2-methyl-(E)-2-butenylidene)-p-toluenesulfinimine (prepared according to Davis F. A. et al. *Tetrahedron Lett.* 1993, 34, 6229) for (S)-(+)-N-benzylidene-p-toluenesulfinimine, and conducting the flash chromatography with ethyl acetate:n-pentane (ratio 3:7) provided the titled compound (61%) as an oil: $|\alpha|_D^{20}$ +76.6° (c 1.0, CHCl$_3$); IR (neat): 2951.2, 1753.2, 1596.0, 1201.8, 1176.4, 1098.5, 1074.0 cm$^{-1}$; $^1$H NMR (CHCl$_3$) δ1.63 (d, J=0.9 Hz, 3H), 1.66 (s, 3H), 2.39 (s, 3H), 3.21–3.30 (m, 2H), 3.54 (s, 3H), 5.57–5.58 (m, 1H), 7.32 (d, J=8.3 Hz, 2H), 7.66 (d, J=8.3 Hz, 2H); $^{13}$C NMR (CDCl$_3$) δ166.8, 141.8, 140.9, 129.5, 126.8, 125.0, 124.3, 51.9, 44.4, 33.3, 21.3, 13.8, 13.1.

Example 7

Methyl (2S,3S)-(+)-3-phenyl-1H-aziridine-2-carboxylate

Into a 50-mL round-bottomed flask equipped with a magnetic stir bar were placed 0.315 g (1.0 mmol) (2S,3S)-(+)-N-(p-toluenesulfinyl)-2-carbomethoxy-3-phenylaziridine (prepared according to Example 1), 5 mL acetone, 5 mL water and 0.4 mL (5 mmol) trifluoroacetic acid. After stirring vigorously for 15 min. at room temperature, the solvent was removed in vacuo. The residue was taken up in 5 mL water, and washed with diethyl ether (2×5 mL). The aqueous layer was brought to pH 10 with concentrated NH$_4$OH and extracted with CH$_2$Cl$_2$ (3×10 mL). The organic phase was dried (MgSO$_4$), filtered and concentrated to give a solid which was purified by flash chromatography (ethyl acetate:n-hexane, 3:7) to give the titled compound (0.147 g, 83%): mp 58° C., (mp 51°–57° C. according to Thijs, L. et al. *Tetrahedron* 1990, 46, 2611); $[\alpha]_D^{20}$ +20.9° (c 1.98, ethanol), ($[\alpha]_D^{20}$ +22.0° (c 1.0, ethanol) according to Thijs, L. et al. *Tetrahedron* 1990, 46, 2611); $^1$H NMR (CDCl$_3$) δ1.73 (bs, 1H, NH), 3.04 (d, J=6.3 Hz, 1H, CH), 3.50 (d, J=6.4 Hz, 1H, CH), 3.52 (s, 3H, CH$_3$), 7.32–7.26 (m, 5H, aromatic); $^{13}$C NMR (CDCl$_3$) δ37.2, 40.2, 52.0, 127.3, 127.6, 128.0, 134.7, 160.3.

Example 8

Methyl (2S,3S)-(+)-3-isopropyl-1H-aziridine-2-carboxylate

The procedure of Example 7 was repeated, but (2S,3S)-(+)-N-(p-toluenesulfinyl)-2-carbomethoxy-3-phenylaziridine was replaced with (2S,3S)-(+)-N-(p-toluenesulfinyl)-2-carbomethoxy-3-isopropylaziridine (prepared according to Example 4) to afford the titled compound (85%) as an oil: $[\alpha]_D^{20}$ +50.2° (c 2.9, CHCl$_3$); IR (KBr): 3265.6, 2960.2, 1734.4, 1208.1 cm$^{-1}$; $^1$H NMR (CDCl$_3$) δ0.91 (d, J=6.7 Hz, 3H), 1.11 (d, J=6.6 Hz, 3H), 1.42–1.52 (m, 2H), 1.96–2.02 (m, 1H), 2.72 (d, J=6.3 Hz, 1H), 3.77 (s, 3H); $^{13}$C NMR (CDCl$_3$) δ171.2, 52.2, 45.5, 34.7, 28.0, 21.1, 20.4. Anal. Calcd for C$_7$H$_{13}$NO$_2$: C, 58.72; H, 9.15. Found: C, 58.40; H, 8.86.

Example 9

Methyl (2S,3S)-(+)-2-amino-3-hydroxy-3-phenylpropanoate

Into a 50-mL round-bottomed flask equipped with a magnetic stir bar were placed 0.315 g (1.0 mmol) (2S,3S)-(+)-N-(p-toluenesulfinyl)-2-carbomethoxy-3-phenylaziridine (prepared according to Example 1), 10 mL acetonitrile and 2 mL 50% aqueous trifluoroacetic acid. The reaction mixture was stirred for 6 h at 45° C., the solvent was removed and the residue treated with H$_2$O (5 mL). After washing the aqueous solution with ether (2×10 mL), the aqueous phase was brought to pH 10 with concentrated NH$_4$OH and extracted with CHCl$_3$ (2×10 mL). After drying (MgSO$_4$), the organic phase was filtered and concentrated to give the titled compound in impure form, which was purified by flash chromatography (ether:CH$_3$CN:NH$_4$OH; 10:1:0.2) to afford the titled compound (0.138 g, 71%) as a viscous oil: $[\alpha]_D^{20}$ +11.0° (c 1.8, MeOH) ($[\alpha]_D^{20}$ −10.97° (c 1.4, MeOH) according to Beulshausen, T. et al. *Liebigs Ann. Chem.* 1991, 1207 for the (2R,3S)-isomer); $^1$H NMR (CDCl$_3$) δ2.10 (bs, 3H, NH$_2$, OH) 3.65 (d, J=4.5 Hz, 1H, CH), 3.69 (s, 3H, CH$_3$), 4.91 (d, J=4.5 Hz, 1H, CH) 7.36–7.26 (m, 5H, aromatic); $^{13}$C NMR (CDCl$_3$) δ52.2, 60.6, 74.1, 126.0, 127.8, 128.4, 140.9, 173.7.

Example 10

Methyl (2S,3R)-(−)-2-amino-3-chloro-3-phenylpropanoate hydrochloride

Into a 50-mL round-bottomed flask equipped with a magnetic stir bar were placed 0.315 g (1.0 mmol) (2S,3S)-(−)-N-(p-toluenesulfinyl)-2-carbomethoxy-3-phenylaziridine (prepared according to Example 1) and 10 mL freshly distilled methanol. The solution was cooled to 0° C. and 2 mL of 5N HCl were added dropwise. The reaction mixture was brought to room temperature and stirred for 1 h. The solvent was removed on a rotary evaporator, the residue was dissolved in 5 mL of H$_2$O and washed with ether (3×10 mL). The aqueous solution was concentrated on a rotary evaporator and dried overnight using a high vacuum pump to give the titled compound (0.178 g, 81%): mp 160°–162° C.; $[\alpha]_D^{20}$ −45.47° (c 1.7, MeOH); IR (KBr): 3300–2600, 1765, 1580, 1485, 1330, 1280, 1150, 1055 cm$^{-1}$; $^1$H NMR (DMSO-d$_6$) δ3.52 (s, 3H, CH$_3$), 4.69 (d, J=7.8 Hz, 1H, N—CH), 5.54 (d, J=7.8 Hz, 1H, O—CH), 7.49–7.39 (m, 5H, aromatic), 9.15 (bs, 3H, NH); $^{13}$C NMR (DMSO-d$_6$) δ52.8, 58.2, 60.3, 127.6, 128.5, 129.2, 135.0, 166.0. Anal. Calcd for C$_{10}$H$_{13}$Cl$_2$NO$_2$: C, 48.02; H, 5.26. Found: C, 47.93; H, 5.30.

Example 11

11A. (2S,3S)-(+)-N-(p-Toluenesulfonyl)-2-carbomethoxy-3-phenylaziridine

Into a 25-mL single-necked round-bottomed flask equipped with a magnetic stir bar were placed 0.63 g (2.0 mmol) of (2S,3S)-(+)-N-(p-toluenesulfinyl)-2-carbomethoxy-3-phenylaziridine (prepared according to Example 1), 1.04 g (3.0 mmol) 3-chloroperoxybenzoic acid (60%, from Aldrich) and 20 mL chloroform. The reaction mixture was stirred at room temperature for 1 h, washed with 20 mL saturated aqueous Na$_2$S$_2$O$_3$ solution, diluted with 50 mL $CH_2Cl_2$, washed with saturated aqueous $Na_2CO_3$ solution (2×10 mL) and dried ($MgSO_4$). Filtration and removal of the solvent gave a solid residue which was purified by flash chromatography (ethyl acetate:n-pentane, 2:8) to afford the titled compound (0.62 g, 94%): mp. 85°–87° C.; $[\alpha]_D^{20}$ +18.2° (c 1.0, $CHCl_3$); IR (KBr): 3033.3, 1757.2, 1597.5, 1334.1, 1210.1, 1163.6, 1091.7 $cm^{-1}$; $^1H$ NMR ($CDCl_3$) $\delta$2.44 (s, 3H, $CH_3$), 3.49 (s, 3H, $CH_3$), 3.71 (d, J=7.7 Hz, 1H, CH), 4.12 (d, J=7.6 Hz, 1H, CH), 7.20–7.32 (m, 5H, aromatic), 7.35 (d, J=8.4 Hz, 2H, aromatic), 7.92 (d, J=8.3 Hz, 2H, aromatic); $^{13}C$ NMR ($CDCl_3$) $\delta$164.5, 145.0, 133.8, 130.9, 129.7, 128.3, 128.0, 127.9, 127.2, 52.3, 45.3, 43.3, 21.6. Anal. Calcd for $C_{17}H_{17}NO_4S$: C, 61.61; H, 5.17. Found: C, 61.43; H, 5.17.

11B. Methyl (2S,3R)-(−)-2-N-(p-toluenesulfonyl) amino-3-hydroxy-3-phenylpropionate Into a 50-mL two-necked round-bottomed flask equipped with a magnetic stir bar, rubber septum and reflux condenser were placed 0.331 g (1.0 mmol) (2S,3S)-(+)-N-(p-toluenesulfonyl)- 2-carbomethoxy-3-phenylaziridine (prepared according to Example 11A), 6 mL dioxane, 4 mL water and 0.1 mL trifluoroacetic acid. The reaction mixture was stirred at 100° C. for 24 h, then cooled to room temperature, diluted with 25 mL ethyl acetate, washed with saturated aqueous $NaHCO_3$ solution (5 mL) and 5 mL brine. The organic phase was dried ($MgSO_4$), filtered and concentrated to give a white solid which was purified by flash chromatography (ethyl acetate:n-hexane, 50:50) to afford the titled compound (0.31 g, 89%) as an 84:16 mixture of syn:anti diastereomers.

Recrystallization from ethyl acetate afforded the purified syn diastereomer (0.21 g, 61%): mp 160°–2° C.; $[\alpha]_D^{20}$ −4.7° (c 0.94, MeOH); IR (KBr): 3600–3250, 1740 1334 1085 $cm^{-1}$; $^1H$ NMR ($CDCl_3$) $\delta$2.38 (s, 3H, $CH_3$), 3.50 (s, 3H, $CH_3$), 4.09 (dd, J=4.0, 9.8 Hz, 1H, N—CH), 5.02 (t, J=3.8 Hz, 1H, O—CH), 5.34 (d, J=9.9 Hz, 1H, NH), 7.16 (d, J=8.1 Hz, 2H, aromatic), 7.27 (m, 5H, aromatic), 7.51 (d, J=8.2 Hz, 2H, aromatic); $^{13}C$ NMR ($CDCl_3$) $\delta$21.6, 54.6, 61.9, 74.2, 126.0, 127.0, 128.2, 128.3, 129.4, 160.1, 182.3. Anal. Calcd for $C_{17}H_{19}NO_5S$: C, 58.43; H, 5.48. Found: C, 58.18; H, 5.38.

Example 12

12A. (2S,3S)-(+)-N-(p-Toluenesulfonyl)-2-carbomethoxy-3-isopropylaziridine

Following the procedure of Example 11A, but replacing the (2S,3S)-(+)-N-(p-toluenesulfinyl)-2-carbomethoxy-3-phenylaziridine with (2S,3S)-(+)-N-(p-toluenesulfinyl)-2-carbomethoxy-3-isopropylaziridine (prepared according to Example 4), and performing the flash chromatography with ethyl acetate:n-pentane (2:8) as the eluent afforded the titled compound (0.565 g, 95%): mp 52°–4° C.; $[\alpha]_D^{20}$ −34.3° (c 1.2, $CHCl_3$); IR (KBr): 2963.9, 1755.8, 1597.5, 1209.6 1102.1, 1091.4 $cm^{-1}$; $^1H$ NMR ($CDCl_3$) $\delta$0.84 (d, J=6.6 Hz 3H), 0.89 (d, J=6.8 Hz, 3H), 1.57–1.68 (m 1H), 2.45 (s, 3H), 2.68 (dd, J=7.6 Hz, 9.9 Hz, 1H), 3.45 (d, J=7.44 Hz, 1H),3.74 (s, 3H), 7.35 (d, J=8.2 Hz, 2H), 7.86 (d, J=8.3 Hz, 2H); $^{13}C$ NMR ($CDCl_3$) $\delta$145.0, 134.0, 129.7, 128.3, 52.6, 50.8, 41.1, 26.7, 21.6, 20.5, 18.9. Anal. Calcd for $C_{14}H_{19}NO_4S$: C, 56.55; H, 6.44. Found: C, 56.36; H, 6.63.

12B. Methyl (2S,3R)-(+)-2-N-(p-toluenesulfonyl) amino-3-formyloxy-4-methylpentanoate Into a 50-mL two-necked round-bottomed flask equipped with a magnetic stir bar, rubber septum and a reflux condenser were placed 0.029 mg (0.1 mmol) (2S,3S)-(+)-N-(p-toluenesulfonyl)-2-carbomethoxy-3-isopropylaziridine (prepared according to Example 12A) and 3 mL formic acid. The resulting mixture was stirred at 100° C. for 1.5 h and concentrated to give a solid which was purified by flash chromatography (ethyl acetate:pentane, 3:7), to afford the titled compound (0.021 g, 63%): mp 114°–115° C.; $[\alpha]_D^{20}$ +73.6° (c 1.3, $CHCl_3$); IR (KBr): 3339.2, 2956.8, 1749.4, 1724.1, 1597.0, 1168.9 1092.2 $cm^{-1}$; $^1H$ NMR ($CDCl_3$) $\delta$0.92 (d, J=6.7 Hz, 3H), 1.00 (d, J=6.7 Hz, 3H), 2.10–2.20 (m, 1H), 2.42 (s, 3H), 3.44 (s, 3H), 4.22 (dd, J=2.1 Hz, 6.8 Hz, 1H), 5.00 (dd, J=1.5 Hz, 9.5 Hz, 1H), 5.19 (d, J=10.7 Hz, 1H), 7.29 (d, J=8.3 Hz, 2H), 7.70 (d, J=8.3 Hz, 2H), 7.96 (s, 1H); $^{13}C$ NMR ($CDCl_3$) $\delta$169.8, 159.7, 143.9, 136.4, 129.6, 127.2, 77.9, 56.1, 52.8, 28.5, 21.5, 18.5, 18.1. Anal. Calcd for $C_{15}H_{21}NO_6S$: C, 52.47; H, 6.16. Found: C, 52.13; H, 6.18.

Example 13
Preparation of thiamphenicol 13A. (+)-(S)-N-(4-Methylthiobenzylidene)-p-toluenesulfinimine Into an oven-dried 100 mL two-necked round-bottomed flask equipped with a magnetic stir bar, rubber septum, and argon-filled balloon were placed (1R,2S,5R)-(−)-menthyl-(S)-p-toluenesulfinate (2.94 g, 10 mmol) and THF (40 mL) cooled to −78° C. Lithium bis(trimethyl)silylamide (1.0M in THF, 15 mL, 15 mmol) was added via syringe, and stirring was maintained for 5 min. at −78° C. and for 5.5 h at room temperature. The solution was cooled to 0° C., and 4-methylthiobenzaldehyde (2.7 mL, 20 mmol) was added via syringe followed by solid CsF (3.0 g, 20 mmol). After stirring for 8 h at room temperature, the solution was quenched with saturated aqueous $NH_4Cl$ solution (10 mL), diluted with ethyl acetate (100 mL) and $H_2O$ (50 mL). The aqueous phase was extracted with ethyl acetate (2×50 mL) and the combined organic phases were washed with $H_2O$ (50 mL), brine (50 mL) and dried ($MgSO_4$). Removal of the solvent gave the crude sulfinimine which was purified by flash chromatography using ethyl acetate:n-hexane (3:7) as the eluent to give 2.3 g (80%) of the titled compound: mp 132°–134° C.; $[\alpha]_D^{20}$ −40.2° (c 1.1, $CHCl_3$); IR (KBr): 1587, 1548, 1495, 1405, 1089 $cm^{-1}$; $^1H$ NMR ($CDCl_3$) $\delta$2.39 (s, 3H), 2.50 (s, 3H), 7.25 (d, J=8.3 Hz, 2H), 7.30 (d, J=8.3 Hz, 2H), 7.62 (d, J=8.3 Hz, 2H), 7.72 (d, J=8.3 Hz, 2H,), 8.68 (s, 1H); $^{13}C$ NMR ($CDCl_3$) $\delta$159.3, 144.9, 141.5, 141.2, 129.8, 129.4, 124.9, 124.4, 21.2, 14.6; Anal. Calcd for $C_{15}H_{15}NOS_2$: C, 62.25; H, 5.22; Found: C, 62.48; H, 5.28.

13B. (2S,3S)-N-(p-Toluenesulfinyl)-2-carbomethoxy-3-(4-methylthiophenyl)aziridine Into a 100-mL oven-dried two-necked round-bottomed flask fitted with a magnetic stir bar, rubber septum and an argon-filled balloon was placed lithium bis(trimethyl) silylamide (1.0M in THF, 7.5 mL, 7.5 mmol) and THF (15 mL). The solution was cooled to −78° C. and methyl α-bromoacetate (0.71 mL, 7.5 mmol) was added via syringe. After stirring for 30 min. at −78° C., a precooled solution (−78° C.) of (S)-(−)-N-(4-methylthiobenzylidene)-p-toluenesulfinimine (0.867, 3.0 mmol) in THF (15 mL) was added via cannula over 30 min. The reaction mixture was stirred for 3 h at −78° C., quenched with water (3 mL) and diluted with ethyl acetate (100 mL). The organic phase was washed with brine (30 mL), dried ($MgSO_4$), filtered and concentrated to give the crude aziridine which was purified by flash chromatography using ethyl acetate:n-hexane (3:7)

as the eluent to give 0.596 g (55%) of the titled compound: mp 86°–88° C.; $[\alpha]_D^{20}$ –2.3° (c 0.5, CHCl$_3$); IR (KBr): 1751, 1592, 1495, 1437, 1095 cm$^{-1}$; $^1$H NMR (CDCl$_3$) δ2.42 (s, 3H), 2.47 (s, 3H), 3.41 (s, 3H), 3.47 (d, J=7.3 Hz, 1H), 3.82 (d, J=7.3 Hz, 1H), 7.20 (d, J=8.2 Hz, 2H), 7.33 (d, J=8.1 Hz, 2H), 7.39 (d, J=8.2 Hz, 2H), 7.70 (d, J=8.1 Hz, 2H); $^{13}$C NMR (CDCl$_3$) δ166.1, 142.3, 140.8, 138.9, 129.8, 129.3, 128.3, 126.1, 125.2, 52.1, 41.9, 34.9, 21.5, 15.6.

13C. (2S,3S)-3-(4-Methylthiophenyl)-1H-aziridine-2-methanol

Into a 50-mL oven-dried two-necked round-bottomed flask fitted with a magnetic stir bar, rubber septum and an argon-filled balloon were placed (2S,3S)-N-(p-toluenesulfinyl)-2-carbomethoxy-3-(4-methylthiophenyl) aziridine (0.362 g, 1.0 mmol) and dry ether (10 mL). The solution was cooled to 0° C., lithium aluminum hydride (0.113 g, 3.0 mmol) was added, the solution was warmed to room temperature, stirred for 1 h, and quenched with saturated aqueous NaHCO$_3$ solution (0.5 mL). The reaction mixture was diluted with ether (30 mL) and the resulting solid collected by filtration and washed with ether (3×40 mL). Concentration of the filtrate gave a light yellow solid which was triturated with ether (10 mL) and the resulting white crystals were collected by filtration to give 0.15 g of the titled compound, with an additional 0.020 g of the titled compound being recovered from the mother liquor, 0.17 g (87%): mp 125°–125° C.; $[\alpha]_D^{20}$ +96.8° (c 0.7, CHCl$_3$); IR (KBr): 3258, 3140, 1600, 1496, 1039 cm$^{-1}$; $^1$H NMR (CDCl$_3$) δ1.84 (br, 2H), 2.48 (s, 3H), 2.64 (m, 1H), 3.25 (m, 1H), 3.44 (m, 2H), 7.24 (qAB, J=8.6 Hz, 4H); $^{13}$C NMR (CDCl$_3$) δ136.9, 133.5, 127.9, 126.3, 61.4, 37.8, 36.5, 16.0; Anal. Calcd for C$_{10}$H$_{13}$OS: C, 61.51; H, 6.71. Found: C, 61.25; H, 6.63.

13D. (2R,3R)-2-Amino-1-(4-methylthiophenyl)-1,3-propanediol

Into a 15 mL two-necked round-bottomed flask fitted with a magnetic stir bar were placed (2S,3S)-3-(4-methylthiophenyl)-1H-aziridine-2-methanol (0.050 g, 0.256 mmol), THF (1 mL) and water (1 mL). p-Toluenesulfonic acid (0.051 g, 0.269 mmol) was added and the reaction mixture stirred for 30 min. at room temperature. Removal of the solvent gave a residue that was dissolved in water (5 mL), brought to pH 12 by addition of aqueous NaOH (50%) and extracted with CH$_2$Cl$_2$ (4×30 mL). The combined organic phases were dried (Na$_2$SO$_4$) and concentrated to gave 0.050 g (93%) of the titled compound as white crystals: mp 148°–150° C. (149°–151° C. according to Clark, J. E. et al. *Synthesis* 1991, 891); $[\alpha]_D^{20}$ 20.9° (c 1.2, EtOH), ($[\alpha]_D^{20}$ –21° (c 2.5, EtOH) according to Clark, J. E. et al. *Synthesis* 1991, 891); $^1$H NMR (DMSO-d$_6$) δ2.46 (s, 3H), 2.67 (m, 1H), 3.12 (m, 1H), 3.30 (m, 1H), 3.32 (m, 4H), 4.41 (d, J=5.8 Hz, 1H), 7.23 (qAB, J=8.4 Hz, 4H).

13E. (2R,3R)-2-N-(Dichloroacetamido)-1-(4-methylthiophenyl)-1,3-propanediol

Into a 25-mL oven-dried two-necked round-bottomed flask fitted with a magnetic stir bar, rubber septum and an argon-filled balloon were placed (2R,3R)-2-amino-1-(4-methylthiophenyl)-1,3-propanediol (0.039 g, 0.183 mmol), triethylamine (0.08 mL, 0.549 mmol) and dry THF (5 mL). The solution was cooled to 0° C. and dichloroacetyl chloride (0.38 mL, 0.5M in THF, 0.192 mmol) was added via syringe. The reaction mixture was stirred for 2.5 h, quenched with saturated aqueous NaHCO$_3$ solution (5 mL), diluted with CH$_2$Cl$_2$ (50 mL) and the organic phase washed with water (10 mL) and dried (Na$_2$SO$_4$) and filtered. Concentration of the filtrate gave 0.55 g (93%) of the titled compound as a white crystalline solid: mp 111°–113° C. (111.6°–112.6° C. according to Cutler, R. A., et al. *J. Am. Chem. Soc.* 1952, 74, 5475); $[\alpha]_D^{20}$ +11.5° (c, 1.3, EtOH) ($[\alpha]_D^{20}$ +12° (c, 1.0, EtOH), according to Cutler, R. A., et al. *J. Am. Chem. Soc.* 1952, 74, 5475); $^1$H NMR (CDCl$_3$) δ2.19 (br, 1H), 2.48 (s, 3H), 2.90 (br, 1H), 3.92 (m, 2H), 4.08 (m, 1H), 5.13 (d, J=3.0 Hz, 1H), 5.85 (s, 1H), 7.27 (qAB, J=8.4 Hz, 4H).

13F. Thiamphenicol

Into a 10 mL single-necked round-bottomed flask fitted with a magnetic stir bar were placed (2R,3R)-2-N-(dichloroacetamido)-1-(4-methylthiophenyl)-1,3-propanediol (0.016 g, 0.048 mmol), dry THF (3 mL) and 95% m-chloroperoxybenzoic acid (0.023 g, 0.012 mmol). The solution was stirred for 1.5 h at room temperature, quenched with saturated aqueous Na$_2$S$_2$O$_3$ solution (5 mL), diluted with CH$_2$Cl$_2$ (50 mL) and the organic phase washed with saturated aqueous Na$_2$CO$_3$ solution (2×5 mL), dried (Na$_2$SO$_4$) and filtered. Concentration of the filtrate gave 0.016 g (95%) of the titled compound as a white solid: mp 164°–166° C., (164.3°–166.3° C. according to Cutler, R. A., et al. *J. Am. Chem. Soc.* 1952, 74, 5475); $[\alpha]_D^{20}$ +12.5° (c, 0.9, EtOH), ($[\alpha]_D^{20}$ +12.9° (c 1.0, EtOH) according to Cutler, R. A., et al. *J. Am. Chem. Soc.* 1952, 74, 5475); $^1$H NMR (DMSO-d$_6$) d 3.15 (s, 3H), 3.28–3.58 (m, 3H), 3.90 (m, 1H), 4.99 (d, J=2.4 Hz, 1H), 6.47 (s, 1H), 7.56 (d, J=8.4 Hz, 2H), 7.83 (d, J=8.4 Hz, 2H), 8.32 (d, J=8.9 Hz, 1H).

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A 2-carboxy-1-sulfinylaziridine compound of general formula (I), the isomers (Ia) or (Ib) and salts thereof

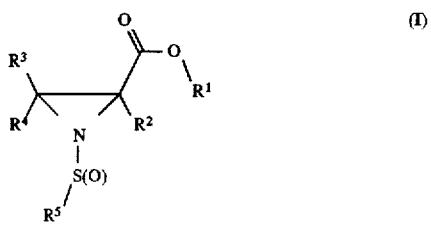

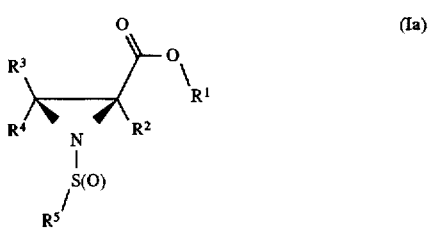

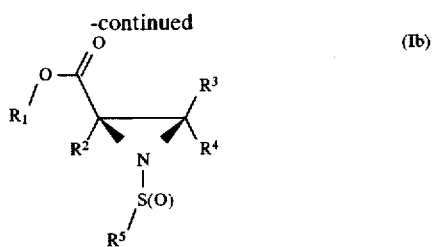

(Ib)

wherein $R^1$, $R^2$, $R^3$, $R^4$ and $R^5$ are independently selected from the group of radicals consisting of hydrogen and a substituted or unsubstituted hydrocarbon radical, said substituted or unsubstituted hydrocarbon radical having from 1–40 carbon atoms, wherein the substituents on or in said substituted hydrocarbon radical are selected from the group consisting of 0–40 halogen atoms, 0–10 heteroatoms selected from the group consisting of boron, nitrogen, oxygen, sulfur, phosphorous, silicon and selenium, with the proviso that $R^3$ and $R^4$ are not simultaneously hydrogen, and S(O) represents a sulfinyl group.

2. A compound according to claim 1 wherein the hydrocarbon radical having from 1 to 40 carbon atoms is selected from the group consisting of aliphatic radicals, aromatic radicals and combinations thereof, where an aliphatic radical comprises acyclic and alicyclic radicals, where the acyclic radical comprises straight- and branched-chain acyclic radicals, where the alicyclic radical comprises bicyclic and other polycyclic radicals, and where the aliphatic or aromatic radical contains 0–10 heteroatoms and 0–40 halogen atoms.

3. A compound according to claim 2 wherein the hydrocarbon radical is a member selected from the group consisting of phenyl, naphthyl, bicyclo[2.2.1]heptyl, $C_1$–$C_{10}$ alkyl, $C_1$–$C_{10}$ alkenyl, $C_3$–$C_{10}$ cycloalkyl, oxazolidyl, pyridyl, pyrazyl, cholesteryl and diacetone-D-glucose, wherein said member may be substituted with 0–7 substituents selected from the group consisting of halogen, nitro, carbonyl, $C_1$–$C_5$ alkoxy, $C_1$–$C_5$ alkyl, hydroxy, phenyl, naphthyl, $C_1$–$C_5$ alkylthio, $C_1$–$C_5$ alkylsulfonyl and benzyloxy.

4. A compound according to claim 3 wherein $R^2$ and $R^4$ are hydrogen.

5. A compound according to claim 4 wherein $R^1$ is $C_1$–$C_{10}$ alkyl, $R^3$ is selected from the group consisting of phenyl, bicyclo[2.2.1]heptyl, $C_1$–$C_5$ alkyl and $C_1$–$C_5$ alkenyl, and wherein the $R^3$ group is substituted with 0–5 substituents selected from the group consisting of $C_1$–$C_5$ alkyl, halogen and nitro.

6. A compound according to claim 2 wherein at least one of $R^2$, $R^3$ or $R^4$ is hydrogen.

7. A compound according to claim 2 wherein either $R^3$ or $R^4$ is hydrogen and the other of $R^4$ or $R^3$ is an aliphatic radical having 1 to 40 carbon atoms containing 0–10 heteroatoms and 0–40 halogen atoms.

8. A compound according to claim 2 wherein either $R^3$ or $R^4$ is hydrogen and the other of $R^4$ or $R^3$ is an aromatic radical substituted with 0–5 $C_1$–$C_8$ aliphatic radicals, where the aliphatic radical and aromatic radical can together contain 0–10 heteroatoms and 0–40 halogen atoms.

9. A compound according to claim 7 wherein $R^2$ is hydrogen.

10. A compound according to claim 8 wherein $R^2$ is hydrogen.

11. A process for preparing a compound according to claim 1 comprising reacting a compound of formula (II) with base to form a reactive intermediate, and then reacting the reactive intermediate with a compound of formula (III), wherein the compounds of formulas (II) and (III) have the structures.

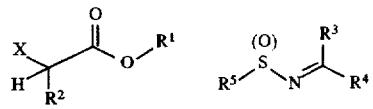

(II)   (III)

wherein X is a leaving group, and $R^1$, $R^2$, $R^3$, $R^4$ and $R^5$ are as defined for compounds of formula (I), and S(O) represents a sulfinyl group in either racemic or optically enriched form.

12. The process according to claim 11 wherein the compound of formula (III) has the structure represented by formula (IIIa) or formula (IIIb)

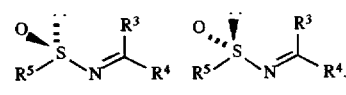

(IIIa)   (IIIb)

13. The process according to claim 11 wherein the reactive intermediate is the enolate of the compound of formula (II) having either 'E' or 'Z' geometry.

14. The process according to claim 11 wherein the base is selected from the group consisting of lithium, sodium or potassium hydride; lithium, sodium or potassium salts of primary, secondary or tertiary amines; sodium amide; lithium alkyls; and metal salts of organic alcohols.

15. The reaction product of treating a compound according to claim 1 with an oxidizing agent, wherein the product of said treatment comprises a compound of formula (VI), or its isomers, compounds of formula (VIa) and (VIb)

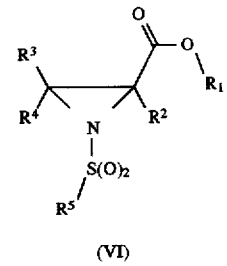

(VI)

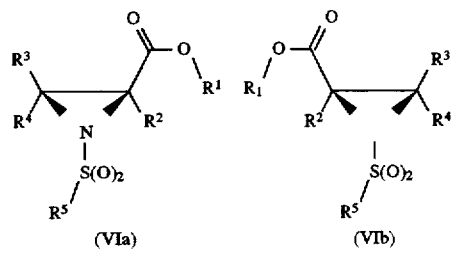

(VIa)   (VIb)

wherein $R^1$, $R^2$, $R^3$, $R^4$ and $R^5$ are defined as for compounds of formula (I).

16. The process according to claim 11 wherein the leaving group is selected from the group consisting of halogen and sulfonate ester.

17. The process according to claim 16 wherein the sulfonate ester is selected from the group consisting of mesylate and tosylate.

* * * * *